United States Patent
Simpson et al.

(10) Patent No.: US 11,440,127 B2
(45) Date of Patent: Sep. 13, 2022

(54) METHODS FOR COUNTERACTING REBOUNDING EFFECTS DURING SOLID STATE RESISTANCE WELDING OF DISSIMILAR MATERIALS

(71) Applicant: Abbott Cardiovascular Systems, Inc., Santa Clara, CA (US)

(72) Inventors: John A. Simpson, Carlsbad, CA (US); Jeffrey F. Dooley, Oceanside, CA (US); Matthew J. Gillick, Murrieta, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 268 days.

(21) Appl. No.: 16/897,784

(22) Filed: Jun. 10, 2020

(65) Prior Publication Data
US 2020/0298332 A1 Sep. 24, 2020

Related U.S. Application Data

(60) Continuation of application No. 15/494,970, filed on Apr. 24, 2017, now Pat. No. 10,717,145, which is a
(Continued)

(51) Int. Cl.
*B23K 11/20* (2006.01)
*A61M 25/09* (2006.01)
(Continued)

(52) U.S. Cl.
CPC ............ *B23K 11/20* (2013.01); *A61M 25/09* (2013.01); *B23K 11/00* (2013.01); *B23K 11/04* (2013.01);
(Continued)

(58) Field of Classification Search
CPC ........ A61M 25/09; A61M 2025/09108; A61M 2025/09091; A61M 2025/09133;
(Continued)

(56) References Cited

U.S. PATENT DOCUMENTS 1,793,218 A    2/1931   Free
2,323,660 A    7/1943   Holt
(Continued)

FOREIGN PATENT DOCUMENTS

CN     1846803     10/2006
EP     1388350     2/2004
(Continued)

OTHER PUBLICATIONS

DC25/UB25 Linear DC Welding Controls, Brochure, Miyachi Unitek Corporation, (2011).
(Continued)

*Primary Examiner* — Brian W Jennison
(74) *Attorney, Agent, or Firm* — Workman Nydegger; Randy Shen

(57) ABSTRACT

The present disclosure is directed to a multi-segment device, such as an intravascular guide wire. The multi-segment device includes an elongate first portion comprising a first metallic material, an elongate second portion comprising a different metallic material, the first and second elongate portions being directly joined together end to end by a solid-state weld, and a heat affected zone surrounding an interface of the weld where the first and second portions are joined together, wherein the heat affected zone has an average thickness of less than about 0.20 mm.

20 Claims, 19 Drawing Sheets

Related U.S. Application Data division of application No. 13/744,276, filed on Jan. 17, 2013, now Pat. No. 9,636,485.

(51) Int. Cl.

| | | |
|---|---|---|
| *B23K 11/00* | (2006.01) | |
| *B23K 11/04* | (2006.01) | |
| *B23K 101/32* | (2006.01) | |
| *B23K 103/02* | (2006.01) | |
| *B23K 103/14* | (2006.01) | |
| *B23K 103/18* | (2006.01) | |
| *B23K 103/04* | (2006.01) | |

(52) U.S. Cl.
CPC ............ A61M 2025/09108 (2013.01); A61M 2025/09133 (2013.01); B23K 2101/32 (2018.08); B23K 2103/02 (2018.08); B23K 2103/05 (2018.08); B23K 2103/14 (2018.08); B23K 2103/26 (2018.08)

(58) Field of Classification Search
CPC ......... A61M 2025/09175; B23K 11/00; B23K 11/04; B23K 11/20; B23K 2101/32; B23K 2101/26; B23K 2101/05; B23K 2103/14; B23K 2103/02; C22C 30/00; C22C 19/056; C22C 19/055; C22C 19/07
See application file for complete search history.

(56) References Cited

U.S. PATENT DOCUMENTS

| | | |
|---|---|---|
| 3,259,969 A | 7/1966 | Tessmann |
| 3,660,176 A | 5/1972 | Denhard, Jr. |
| 3,961,153 A | 6/1976 | Smith et al. |
| 4,358,658 A | 11/1982 | Van et al. |
| 4,478,787 A | 10/1984 | Nadkarni et al. |
| 4,518,444 A | 5/1985 | Albrecht et al. |
| 4,922,924 A | 5/1990 | Gambale et al. |
| 4,934,380 A | 6/1990 | De Toledo |
| 5,124,529 A | 6/1992 | Nishikawa et al. |
| 5,135,503 A | 8/1992 | Abrams |
| 5,354,623 A | 10/1994 | Hall |
| 5,368,661 A | 11/1994 | Nakamura et al. |
| 5,411,476 A | 5/1995 | Abrams et al. |
| 5,415,178 A | 5/1995 | Hsi et al. |
| 5,488,959 A | 2/1996 | Ales |
| 5,630,840 A | 5/1997 | Mayer |
| 5,706,826 A | 1/1998 | Schwager |
| 5,720,300 A | 2/1998 | Fagan et al. |
| 5,769,796 A | 6/1998 | Palermo et al. |
| 5,772,609 A | 6/1998 | Nguyen et al. |
| 5,851,192 A | 12/1998 | Shimura et al. |
| 5,876,783 A | 3/1999 | Dobson |
| 5,916,178 A | 6/1999 | Noone et al. |
| 5,951,886 A | 9/1999 | Schubert et al. |
| 6,001,068 A | 12/1999 | Uchino et al. |
| 6,019,736 A | 2/2000 | Avellanet et al. |
| 6,248,082 B1 | 6/2001 | Mo |
| 6,267,776 B1 | 7/2001 | O'Connell |
| 6,306,105 B1 | 10/2001 | Rooney et al. |
| 6,379,392 B1 | 4/2002 | Walak |
| 6,387,060 B1 | 5/2002 | Jalisi |
| 6,602,208 B2 | 8/2003 | Jafari |
| 6,645,159 B1 | 11/2003 | Burkett |
| 6,669,652 B2 | 12/2003 | Anderson et al. |
| 6,702,762 B2 | 3/2004 | Jafar et al. |
| 6,729,526 B2 | 5/2004 | Okamoto et al. |
| 6,736,843 B1 | 5/2004 | Fariabi |
| 6,799,067 B2 | 9/2004 | Pacetti et al. |
| 6,866,642 B2 | 3/2005 | Kellerman et al. |
| 6,918,882 B2 | 7/2005 | Skujins et al. |
| 7,547,288 B2 | 6/2009 | Murayama et al. |
| 7,627,382 B2 | 12/2009 | Minar et al. |
| 7,722,552 B2 | 5/2010 | Aimi et al. |
| 7,785,273 B2 | 8/2010 | Alan |
| 7,785,274 B2 | 8/2010 | Mishima et al. |
| 7,896,820 B2 | 3/2011 | Satou et al. |
| 8,083,689 B2 | 12/2011 | Vrba |
| 8,721,564 B2 | 5/2014 | Simpson et al. |
| 9,061,088 B2 | 6/2015 | Simpson |
| 2002/0179202 A1 | 12/2002 | Kautz et al. |
| 2003/0220677 A1 | 11/2003 | Doan et al. |
| 2004/0030265 A1 | 2/2004 | Murayama et al. |
| 2004/0039309 A1 | 2/2004 | Murayama et al. |
| 2004/0167442 A1 | 8/2004 | Shireman et al. |
| 2004/0167443 A1 | 8/2004 | Shireman et al. |
| 2004/0181176 A1 | 9/2004 | Jafari et al. |
| 2004/0182835 A1 | 9/2004 | Hall |
| 2004/0217092 A1 | 11/2004 | Demers et al. |
| 2004/0260206 A1 | 12/2004 | Murayama et al. |
| 2005/0051243 A1 | 3/2005 | Forbes et al. |
| 2005/0137501 A1 | 6/2005 | Euteneuer et al. |
| 2005/0150871 A1 | 7/2005 | Offer |
| 2005/0256563 A1 | 11/2005 | Clerc et al. |
| 2006/0047223 A1 | 3/2006 | Grandfield et al. |
| 2006/0122537 A1 | 6/2006 | Reynolds et al. |
| 2006/0259063 A1 | 11/2006 | Bates et al. |
| 2007/0010762 A1 | 1/2007 | Ressemann et al. |
| 2007/0034607 A1 | 2/2007 | Scott et al. |
| 2007/0199607 A1 | 8/2007 | Murayama et al. |
| 2007/0244413 A1 | 10/2007 | Biggins |
| 2007/0282270 A1 | 12/2007 | Mathews et al. |
| 2008/0171952 A1 | 7/2008 | Mishima |
| 2009/0036834 A1 | 2/2009 | Voeller et al. |
| 2009/0221935 A1 | 9/2009 | Murayama et al. |
| 2009/0227902 A1 | 9/2009 | Simpson et al. |
| 2009/0318835 A1 | 12/2009 | Ressemann et al. |
| 2010/0075168 A1 | 3/2010 | Schaffer |
| 2010/0119870 A1 | 5/2010 | Nojiri et al. |
| 2010/0233501 A1 | 9/2010 | Messer et al. |
| 2011/0278264 A1 | 11/2011 | Murayama et al. |
| 2011/0287031 A1 | 11/2011 | Paul et al. |
| 2011/0295155 A1 | 12/2011 | Simpson et al. |
| 2012/0228273 A1 | 9/2012 | Mishima et al. |
| 2012/0283700 A1 | 11/2012 | Pawluk |
| 2012/0305533 A1 | 12/2012 | Matteson |
| 2014/0200555 A1 | 7/2014 | Simpson et al. |
| 2014/0246407 A1 | 9/2014 | Simpson et al. |
| 2015/0231370 A1 | 8/2015 | Simpson |

FOREIGN PATENT DOCUMENTS

| | | |
|---|---|---|
| GB | 1552165 A | 9/1979 |
| JP | 06-328262 A | 11/1994 |
| JP | 2003-049249 A | 2/2003 |
| JP | 2003-190291 A | 7/2003 |
| JP | 2004-065796 A | 3/2004 |
| JP | 2004-065797 A | 3/2004 |
| JP | 2004-230140 A | 8/2004 |
| JP | 2004-230142 A | 8/2004 |
| JP | 2004-292174 A | 10/2004 |
| JP | 2005-177094 A | 7/2005 |
| JP | 2006-519072 A | 8/2006 |
| JP | 2008-264872 A | 11/2008 |
| JP | 2011-152467 A | 8/2011 |
| JP | 2012-502190 A | 1/2012 |
| JP | 2013-027914 A | 2/2013 |
| WO | 03/57273 | 7/2003 |
| WO | 2004/033016 A1 | 4/2004 |
| WO | 2006/002199 A2 | 1/2006 |
| WO | 2008/123402 A1 | 10/2008 |
| WO | 2013/116379 A1 | 8/2013 |

OTHER PUBLICATIONS

EWI, "EWI's Nitinol-Stainless Steel Welding Process Enables More Advanced Applications of Shape Memory Alloys," Insights Materials Joining Newsletter, p. 6, Winter 2004, vol. 17, No. 1.
Fort Wayne Metals "Precision Wire. Drawn to your specifications." 2011, p. 2.3.
Fort Wayne Metals Resource Library, 35N LT excerpt from Fort Wayne Metals Research Products website, 3 pages.

(56) References Cited

OTHER PUBLICATIONS

Fort Wayne Metals, Research Products Corp., 2011, pp. 1-43.
Frenchick, Grady J., Third-Party Preissuance Submission under 37CFR .sctn. 1.290, 15 pages.
Improving Resistance Welding Process Control in Medical Applications, MDDI Medical Device and Diagnostic Industry Magazine, Nov. 1, 1997, p. 1-9.
MEA-100 AC Resistance Welding Power Supply, Technical Data Sheet, Miyachi Europe Corporation, Jul. 2012, pp. 1-3.
Notice of Allowance received for U.S. Appl. No. 13/364,548, dated Mar. 3, 2015.
Notice of Allowance received for U.S. Appl. No. 13/744,276, dated Jan. 19, 2017.
Notice of Allowance received for U.S. Appl. No. 13/892,959, dated Jan. 7, 2014.
Office Action received for U.S. Appl. No. 13/364,548, dated Dec. 4, 2014.
Office Action received for U.S. Appl. No. 13/364,548, dated Feb. 21, 2014.
Office Action received for U.S. Appl. No. 13/364,548, dated Jul. 31, 2014.
Office Action received for U.S, U.S. Appl. No. 13/744,276, dated Apr. 2, 2015.
Office Action received for U.S. Appl. No. 13/744,276, dated Mar. 9, 2016.
Office Action received for U.S. Appl. No. 13/744,276, dated Nov. 2, 2016.
Office Action received for U.S. Appl. No. 13/744,276, dated Sep. 3, 2015.
Office Action received for U.S. Appl. No. 13/892,959, dated Jul. 5, 2013.
Office Action received for U.S. Appl. No. 13/892,959, dated Oct. 28, 2013.
Office Action received for U.S. Appl. No. 14/703,391, dated Apr. 18, 2017.
Office Action received for U.S. Appl. No. 14/703,391, dated Dec. 12, 2016.
Ryhanen, J., "Fundamental chracteristics of nickel-titanium shape memory alloy," Biocampatibility Evaluation of Nickel-titanium Shape memory Metal Alloy, Academic Dissertation presented at University Hospital of Oulu, May 7, 1999, pp. 24-31.
United States Patent and Trademark Office, 35N LT Registration Summary, 1 page.
Wang, G., "Welding of Nitinol to Stainless Steel," Proceedings of the second International Conference on Shape Memory and Superelastic Technologies, 1996, p. 131-136, Asilomar Conference Center, Pacific Grove, California.
Zapp Precision Wire Alloy MP35N (UNS R30035) Wire, Zapp Precision Wire, Inc., Accessed Jan. 13, 2014, pp. 1-4, Summerville, South Carolina.

METHODS FOR COUNTERACTING REBOUNDING EFFECTS DURING SOLID STATE RESISTANCE WELDING OF DISSIMILAR MATERIALS

CROSS-REFERNCE TO RELATED APPLICATIONS

This application is a continuation of U.S. patent application Ser. No. 15/494,970, filed 24 Apr. 2017, which is a divisional of U.S. patent application Ser. No. 13/744,276, filed 17 Jan. 2013, now U.S. Pat. No. 9,636,485, the disclosures of which are incorporated herein by reference in their entireties.

BACKGROUND

The human body includes various lumens, such as blood vessels or other passageways. A lumen may sometimes become at least partially blocked or weakened. For example, a lumen may be at least partially blocked by a tumor, by plaque, or both. An at least partially blocked lumen may be reopened or reinforced with an implantable stent.

A stent is typically a tubular body that is placed in a lumen of the body. A stent may be delivered inside the body by a catheter that supports the stent in a reduced-size configuration as the stent is delivered to a desired deployment site within the body. At the deployment site, the stent may be expanded so that, for example, the stent contacts the walls of the lumen to expand the lumen.

A guide wire may be employed when delivering a delivery catheter and stent to a desired location. For example, a guide wire may be advanced through a guiding catheter until the distal tip of the guide wire extends just beyond the location where the stent is to be implanted. A catheter and a stent to be positioned may be mounted onto the proximal portion of the guide wire, and the catheter and stent may be advanced over the guide wire until the catheter and stent are disposed within the blood vessel or other passageway where the stent is to be implanted. Once the stent is implanted, the catheter may be withdrawn over the guide wire. The guide wire may also be withdrawn.

Guide wires may often include an elongate core member with one or more segments near the distal end which taper distally to smaller cross-sections. A helical coil or other flexible body member may be disposed about the distal end of the guide wire. A shaping member, which may be at the distal extremity of the core member, may extend through the flexible body and be secured to the distal end of the flexible body by soldering, brazing, welding, an adhesive, etc. The leading tip of the structure may be highly flexible in order not to damage or perforate the blood vessel or other passageway. The portion proximal to the distal tip may be increasingly stiff, to provide the ability to support a balloon catheter or similar device.

One major requirement for guide wires is that they provide sufficient column strength to be pushed through the patient's vasculature or other body lumen without buckling. On the other hand, they must be sufficiently flexible to avoid damaging the body lumen as they are advanced. Efforts have been made to improve both strength and flexibility of guide wires to make them more suitable for these purposes, although these two desired characteristics are generally diametrically opposed to one another, such that an improvement in one typically results in less satisfactory performance relative to the other.

Despite a number of different approaches for addressing these issues, there still remains a need for improved guide wires and associated methods of manufacture.

SUMMARY

For instance, in one configuration, the present disclosure is directed to methods for joining members of different metallic materials that are incompatible with one another. In one embodiment, multiple initially separate members are provided, which members comprise different materials (e.g., one member may comprise a nickel-titanium alloy such as nitinol, while another member may comprise stainless steel). The separate members are aligned with one another, and a first force is applied while delivering electrical (e.g., DC, AC, or both) current through the separate members so as to weld the separate portions to one another. During welding, the applied electrical (e.g., DC, AC, or both) current serves to heat the portions of the members to be joined so that they undergo solid state deformation, such that the materials are not melted, but deform and form a weld joint while in a solid state. A follow up force that is greater than the first force is applied to the members as deformation of the members occurs. The deformation results in formation of a weld nugget between the members. Because of application of the follow up force, the nugget is thinner and of a larger transverse cross-sectional area than would be produced without application of the follow up force. In an embodiment, the follow up force may be applied after some (e.g., most or all) electrical weld energy has been delivered (e.g., after current delivery stops), but before deformation (i.e., setdown) has been completed. In an embodiment, the method may be employed to join separate elongate segments or portions of an intravascular guide wire to one another, end-to-end.

Application of a follow up force, rather than increasing the amount of weld energy applied (e.g., in the form of DC or AC current) acts to increase solid state deformation (i.e., forging) without having to raise the temperature of the weld material via input of additional weld energy. This in effect avoids an undesirable tradeoff associated with increasing solid state deformation to enlarge and flatten the weld nugget by increasing electrical weld energy input. While an increase in electrical weld energy input may act to increase solid state deformation, it undesirably increases risk of melting, which adversely impacts weld integrity due to metallurgical incompatibility between dissimilar materials such as nitinol and stainless steel. Application of a follow up force that is greater than the baseline force applied during delivery of the electrical weld energy enables weld nugget deformation to be substantially increased while maintaining appropriate temperatures to avoid melting.

One embodiment is directed to a method for joining a multi-segment intravascular guide wire in which multiple initially separate portions of the guide wire are provided, the portions comprising different metallic materials. Each portion includes an end to be joined to a corresponding end of another portion (e.g., the portions may be joined end to end). Corresponding ends of the guide wire portions may be prepared to flatten and smooth the corresponding ends (and to remove any oxide layer) prior to axial alignment and welding. The corresponding ends may be axially aligned with one another, and a first axial force is applied while delivering electrical (e.g., DC, AC, or both) current through the separate guide wire portions to weld the separate guide wire portions to one another. A follow up axial force that is greater than the first axial force is applied after electrical (e.g., DC, AC, or both) current delivery has stopped and before rebounding occurs, as axial deformation of the guide wire portions forms a weld nugget between the guide wire portions. The thus formed weld nugget is thinner and of a larger transverse cross-sectional area than would be produced without application of the follow up axial force.

The methods of manufacture herein described can be used to produce multi-segment intravascular guide wires with distinguishing characteristics as compared to those produced without application of the follow up force. For example, a multi-segment intravascular guide wire may include a first portion comprising a first metallic material, a second portion comprising a second metallic material different from the first material, in which the first and second portions are directly joined together end to end by a weld. A heat affected zone is disposed at the location of the weld where the first and second portions are joined together. The heat affected zone corresponds to the weld nugget, and may typically exhibit hardness characteristics different from adjacent portions of the first and second portions that were not affected by the heat associated with solid state deformation and formation of the weld nugget. The heat affected zone may have a length (e.g., less than 0.20 mm) that is less than a heat affected zone of an otherwise similarly formed multi-segment intravascular guide wire, but formed without application of the follow up force. The shorter heat affected zone may provide increased kink resistance. In addition to the shorter heat affected zone the weld exhibits strength characteristics that are more consistent from one manufactured guide wire to another.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

To further clarify at least some of the advantages and features of the present disclosure, a more particular description of the disclosure will be rendered by reference to various embodiments thereof that are illustrated in the appended drawings. It is appreciated that these drawings depict only various embodiments of the disclosure and are therefore not to be considered limiting of its scope. The various embodiments will be described and explained with additional specificity and detail through the use of the accompanying drawings in which.

DETAILED DESCRIPTION

I. Introduction

Figure 1:
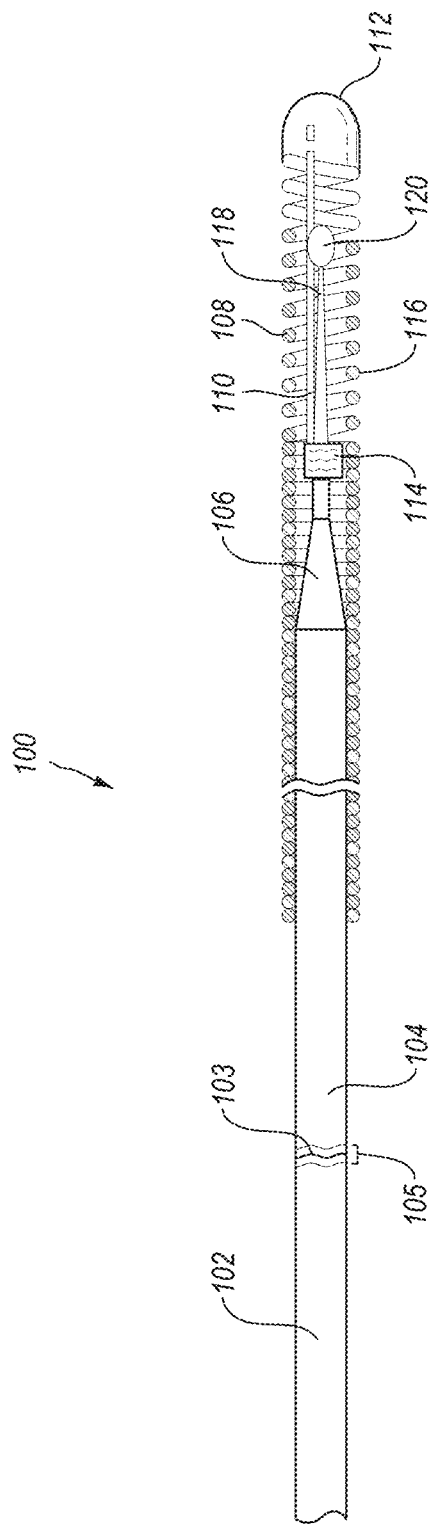
FIG. 1 is a side elevation and partial cross-sectional view of a multi-segment intraluminal guide wire according to an embodiment of the present disclosure.

For instance, in one configuration, the present disclosure is directed to methods for joining members of different metallic materials. The method includes providing multiple initially separate members, which members comprise different metallic materials (e.g., nitinol and stainless steel). The separate members are aligned with one another, and a first force is applied while delivering electrical (e.g., DC, AC, or both) current through the separate members to weld the separate members to one another. A follow up force that is greater than the first force is applied as solid-state deformation occurs and a weld nugget forms between the members. The resulting weld nugget is thinner and of a larger transverse cross-sectional area than would be produced without application of the follow up force. The method may be employed to join separate elongate segments or portions of an intravascular guide wire to one another, end-to-end.

The present manufacturing methods may be employed with respect to any desired medical or other devices where it is desired to join two dissimilar metals together with a weld formed under solid state deformation conditions, without melting the materials. For example, when joining members comprising dissimilar, and possibly incompatible metals (e.g., titanium in one segment and iron in another member), melting of the metal members during a welding procedure can result in formation of brittle, undesirable intermetallic compounds. Other incompatibilities may similarly present a situation in which it is desired to join two dissimilar metallic members together, while minimizing risk of melting, which for one reason or another may complicate or exacerbate any incompatibilities of the two materials.

While melting is unacceptable, it has also been recognized that direct welding of dissimilar, incompatible materials to one another, such as stainless steel and nitinol has been a practical impossibility. While in theory one might hope to be able to directly join such dissimilar metals together through a welded joint formed under solid state deformation, rather than melting, up to now, this has proven to be a practical impossibility, at least on a commercial scale, while meeting applicable quality control standards. Given these practical difficulties, various techniques have been employed to directly join two such dissimilar materials together. For example, U.S. Pat. No. 7,998,090 describes use of a transition piece (e.g., formed of nickel) employed between the otherwise incompatible segments to indirectly join the two segments together. Another technique may employ an adhesive, rather than a welded joint to connect the dissimilar segments comprising incompatible metals. Such an adhesive joint may include a coupling, which component is relatively costly.

The methods of the present disclosure advantageously provide the ability to directly join two dissimilar metal members (e.g., nitinol and stainless steel) with a weld formed under solid state deformation conditions, while providing a high level of consistency (i.e., reduced or low variability) to the strength of the weld. As such, the method is suitable for commercial use so as to produce a high volume of multi-member components comprising dissimilar metals exhibiting consistent strength characteristics so as to consistently meet desired quality control standards.

II. Example Intravascular Multi-Segment Guide Wires

In an embodiment, the methods are employed to join two segments or portions of a multi-segment guide wire where the segments or portions comprise different metallic materials. The terms segment and portion may be used interchangeably herein to refer to segments or portions of the multi-segment guide wire. FIG. 1 is an elevation side view and partial cross-section view of a guide wire 100 including features according to the present disclosure. Guide wire 100 may be adapted for insertion into a body lumen of a patient, for example a vein or artery. Guide wire 100 may include an elongate, relatively high strength proximal core portion 102 directly welded to a relatively flexible distal core portion 104 at weld joint 103. Weld joint 103 may be surrounded by a heat affected zone 105 as will be described below. Distal core portion 104 may include a tapered section 106, tapering to a smaller thickness in the distal direction. A helical coil 108 may be disposed about distal core section 104, which may be secured by its distal end to a distal end of shaping ribbon 110 (e.g., by solder) near rounded plug 112.

A proximal end of shaping ribbon 110 may be secured (e.g., by solder) to distal core portion 104 at the same or a nearby location 114. A distal section 116 of coil 108 may be stretched in length to provide additional flexibility. Distal tip 118 of distal core portion 104 may be flattened into a rectangular cross-section, and may include a rounded tip 120 (e.g., solder) to prevent passage of distal tip 118 through any spaces between the coils of helical coil 108.

Figure 2:
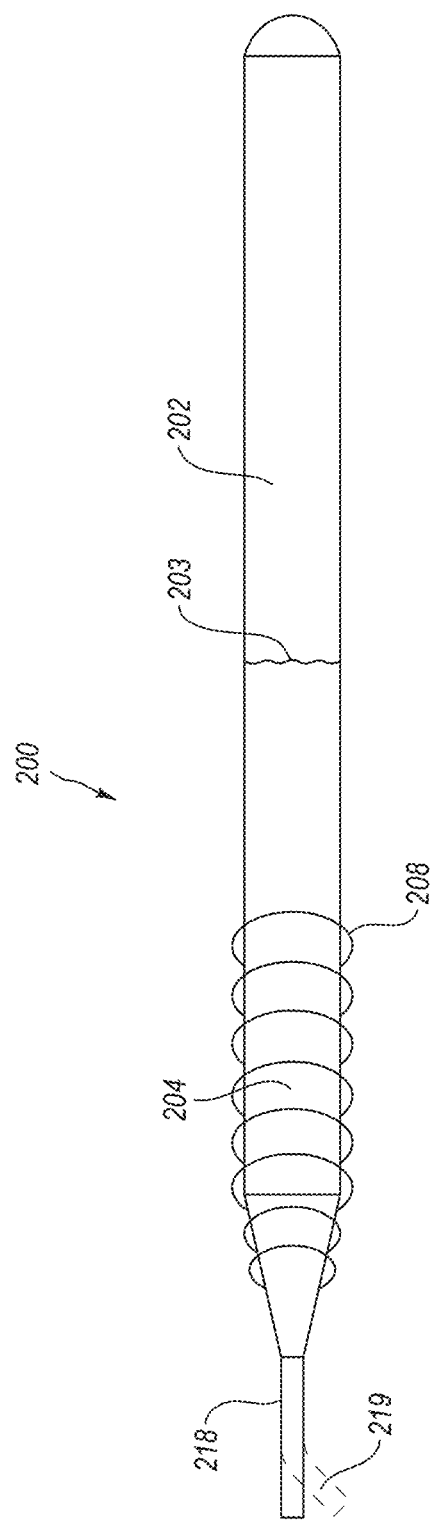
FIG. 2 is a simplified side elevation view of a multi-segment core-to-tip intraluminal guide wire according to an embodiment of the present disclosure.

FIG. 2 shows a simplified embodiment of another intravascular guide wire 200 including features of the present disclosure. Core portions 202 and 204 may be directly welded together at weld joint 203 during fabrication. Similar to guide wire 100, weld joint 203 includes a heat affected zone surrounding joint 203 as a result of the solid state deformation of the materials within this region. Portion 202 may comprise a material (e.g., stainless steel) having a relatively higher modulus of elasticity. A distal end of portion 202 may be directly joined through a weld (e.g., a butt weld) formed through solid state deformation to distal portion 204, which comprises a different material (e.g., nitinol), having a relatively lower modulus of elasticity. Distal portion 204 may include a flattened, shapeable distal tip 218 which can be permanently deformed (e.g., by finger pressure) to create a tip that can be steered through a patient's vasculature. As shown, distal tip 218 may be bent or deformed into a J, L or similar bend 219. A tip coil 208 may be disposed over distal core portion 204.

The illustrated configurations for guide wires 100, 200 are merely two of many possible configurations, and other guide wire configurations including multiple segments that may be directly joined together by a weld formed under solid state deformation conditions are encompassed by the present disclosure.

Distal core section 104, 204 may be made of a nickel-titanium alloy such as nitinol, a pseudoelastic alloy including about 30 atomic percent to about 52 atomic percent titanium, with the balance typically being nickel. Optionally, up to about 10 atomic percent or up to about 3 atomic percent of one or more other alloying elements may be included. Other alloying elements include, but are not limited to iron, cobalt, vanadium, platinum, palladium, copper, and combinations thereof. Where copper, vanadium, or combinations thereof are included, each may be included in amounts of up to about 10 atomic percent in one embodiment. In one embodiment, where iron, cobalt, platinum, palladium, or combinations thereof are included, each may be included in amounts of up to about 3 atomic percent.

Addition of nickel above equiatomic amounts relative to titanium increases stress levels at which the stress induced austenite to martensite transition occurs. This characteristic can be used to ensure that the temperature at which the martensitic phase thermally transforms to the austenitic phase is well below human body temperature (37° C.) so that the austenite is the only temperature stable phase at body temperature. Excess nickel may also provide an expanded strain range at very high stresses when the stress induced transition occurs during use.

Because of the extended strain range characteristic of nitinol, a guide wire having a distal portion made at least in substantial part of such material can be readily advanced through tortuous arterial passageways with minimal risk of kinking. Such characteristics are similarly beneficial where the distal nitinol portion of the guide wire may be prolapsed, either deliberately or inadvertently.

The proximal portion 102, 202 of guide wire 100, 200 may typically be significantly stronger (i.e., having higher tensile strength) than pseudoelastic distal portion 104, 204. For example, proximal portion 102, 202 may be formed of stainless steel (e.g., SAE 304 stainless steel). Other high strength materials, including, but not limited to cobalt-chromium alloys such as MP35N may also be employed.

As described above, prior attempts to directly weld such incompatible, dissimilar materials to one another have been very challenging, and as a practical matter impossible. For example, even if a weld connection can be made, localized damage within the heat affected zone associated with the weld often results in weld integrity that may be diminished seemingly at random, with no known nondestructive method of detection. Thus, such welded components, even if successfully joined together by welding, have been found to exhibit undesirably high variations in weld strength, which can lead to unpredictable failure of the weld prior to, or worse yet, during use.

Because of these difficulties in directly welding such dissimilar and incompatible materials together, such direct weld connections have been avoided. Rather, the dissimilar, incompatible segments have been indirectly joined to one another by employing a transition piece positioned between the incompatible materials, or by joining them without resorting to a weld (e.g., use of an adhesive and/or a coupling). Such solutions result in increased complexity and cost. Methods that would provide the ability to directly join dissimilar, incompatible metal materials together through a welded joint, while providing low levels of variability (i.e., high levels of consistency) of weld strength would be a marked advance in the art. The present disclosure describes such methods of manufacture and corresponding multi-segment intravascular guide wires so formed.

III. Embodiments of Methods for Joining Segments of Multi-Segment Intravascular Guide Wires In an embodiment, the present methods may achieve direct joining of dissimilar metal materials to one another through a resistance, solid-state welding process in which the segments may be welded to one another. The welding process achieves the desired direct joint through solid state deformation of the ends of the two segments, without melting of either material. Such a method is particularly advantageous in the field of intravascular guide wires where the wire segments to be welded to one another are relatively small, such that known methods of solid state deformation weld bonding are unsuitable. For example, welding processes capable of reliably joining dissimilar metals together without melting of either work piece are known. Such methods involve solid state bonding, rather than melting and fusion. A metallurgical bond is created while both materials remain in the solid state, typically through application of heat and pressure at the interface of the dissimilar metals.

The earliest developed method, known as forge welding, employs the blacksmith's technique of heating both work pieces near but below their respective melting points and forcing them together via successive hammer blows. Such a method is of course not suitable for welding fine wires together end-to-end, as may be required when joining multiple segments of a multi-segment intravascular guide wire. Another solid state joining method, explosion welding, uses an engineered explosive charge to generate extremely high velocity and resulting high interfacial pressure between the pieces to be joined together. Such a method is employed in laminating sheet and plate materials, although it is not suitable for joining together fine wires.

U.S. Pat. No. 7,998,090 suggests another solid-state bonding technique which the reference describes as a hybrid of resistance welding and friction welding. Even so, this reference concludes that direct connection of dissimilar, incompatible materials such as nitinol and stainless steel is a practical impossibility, relying instead on the placement of a transition piece comprising a third material (e.g., nickel) that exhibits compatibility to both of the dissimilar, incompatible pieces therebetween. As described above, such methods are overly complicated and costly.

Figure 3:
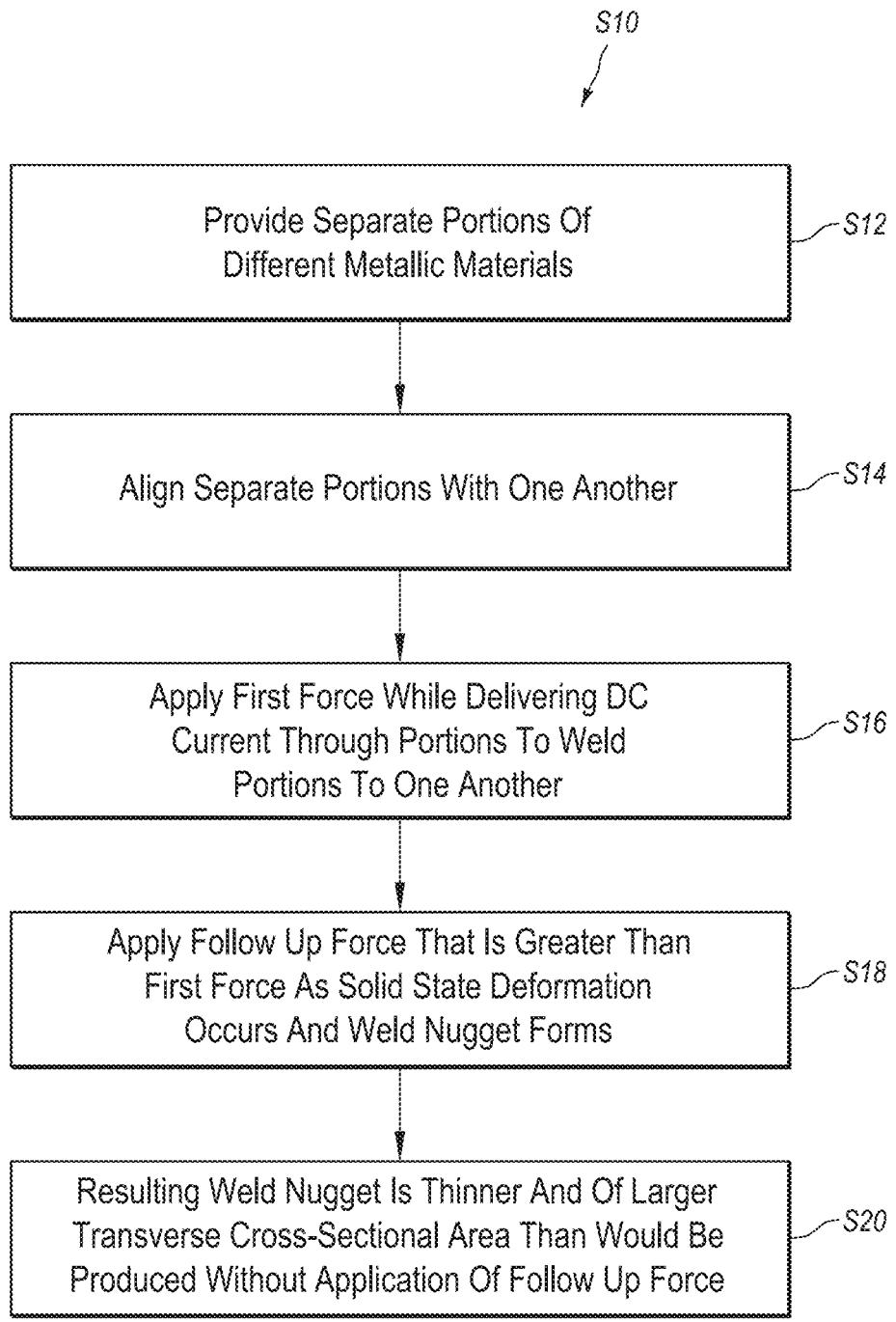
FIG. 3 is a flow chart illustrating a method for joining a multi-segment intravascular guide wire according to an embodiment of the present disclosure.

The present methods overcome the difficulties previously encountered when attempting to directly weld two dissimilar wire segments, for example end-to-end as in a multi-segment guide wire. As shown in FIG. 3, according to method S10, multiple, initially separate portions of the guide wire, each comprising a different material, are provided at S12. Although FIGS. 1 and 2 show embodiments including two segments, it will be understood that the methods herein described may similarly be employed to join more than two segments together, without the need to position any transition piece between the incompatible, dissimilar metal segments for compatibility purposes. For example, were three segments desired, two segments may be joined, followed by joining the resulting structure with a third segment. At S14, the separate portions or segments are aligned (e.g., axially, end-to-end) with one another. As indicated at S16, a first force (e.g., axial) is applied while delivering electrical (e.g., DC, AC, or both) current through the separate guide wire portions to begin directly welding the separate portions or segments to one another. At S18, a follow up force (e.g., axial) that is greater than the first force is applied as solid state deformation occurs, and as the weld nugget forms between the guide wire portions or segments. As indicated at S20, the resulting weld nugget is thinner and of a larger transverse cross-sectional area than would be produced without application of the follow up force. The method has been found to effectively and reliably directly join two dissimilar, incompatible elongate wire segments or portions to one another, while consistently achieving desired strength characteristics.

Prior to aligning the corresponding ends of the separate guide wire portions, the ends to be joined together may be prepared by flattening and smoothing the ends. Such end preparation may be achieved by grinding the mating ends just prior to alignment and the beginning of the welding process (i.e., when the first force is applied and electrical current is delivered through the segments). This may be so, even where the ends may have been smoothed and flattened previously, as removal of any oxide layers at this stage is desirable. According to one such method, the ends may be ground with a rotating disc covered with wet or dry sandpaper. An aqueous grinder coolant may serve to remove debris during the grinding step. Such a flattening and smoothing procedure acts to remove oxide from the wire ends, which oxide may otherwise interfere with the ability to achieve sufficient and consistent weld strength. For example, in the case of nitinol and stainless steel wire segments the nitinol forms a titanium oxide layer, while the stainless steel includes a chromium oxide layer. It is beneficial to remove these oxide layers from the corresponding ends that are to be welded together. Removal of any oxide layers (e.g., preferably performed immediately prior to axial alignment and welding) minimizes contact resistance and reduces variability in contact resistance due to the presence of the oxide layers. This helps reduce variability in weld temperature from one weld to another, which helps in ensuring that no melting of either metal of the dissimilar wire segments occurs.

As used herein, when referring to preparation of the corresponding ends being performed "immediately prior to" or "just prior to" axial alignment and welding, it will be understood that some passage of time between preparation of the corresponding ends of the segments or portions to be joined together and axial alignment and butt welding of the segments or portions is acceptable so long as such time period is sufficiently short so as to prevent reformation of an oxide film over the prepared ends which could affect the contact resistance between said ends. For example, in one embodiment, preparation of the ends is performed within about 1 day of welding, within about 10 hours of welding, within about 1 hour of welding, within about 30 minutes of welding, within about 15 minutes of welding, within about 5 minutes of welding, within about 2 minutes of welding, or within about 1 minute of welding.

In addition, to prevent formation of an oxide layer over the prepared ends during resistance heating, the ends may be tightly pressed together (e.g., about 100,000 psi to about 200,000 psi) through application of the first force prior to application of any electrical (e.g., DC, AC, or both) current so as to prevent any air from being present therebetween that might result in reformation of the oxide layers. If desired, resistance heating and the application of the forces associated with the welding process may be undertaken in an inert environment, which may further aid in preventing formation of any undesirable oxide layers that would interfere with contact resistance and maintaining weld temperature within the desired window.

The baseline first force may be applied axially, and applied at any desired level, which may depend at least in part on the dimensions and material characteristics of the wire segments to be joined together. In one example, the force applied may be from about 1 lb to about 100 lbs, from 5 lbs to 50 lbs, from about 10 lbs to about 30 lbs, or from about 15 lbs to about 25 lbs. Where the process is employed to join relatively thin, elongate wire segments, such levels of force may result in pressures from about 100,000 psi to about 200,000 psi. For example, when joining wire segments each having a diameter of about 0.013 inch and applying a baseline force of 20 lbs, the resulting pressure at the interface is about 150,000 psi.

The baseline force and the cross-sectional thickness of the wire segments may result in a pressure at the interface of the segments from about 35,000 psi to about 400,000 psi, from about 75,000 psi to about 250,000 psi, or from about 100,000 to about 200,000 psi. Wire segments having relatively larger cross-sectional area may be processed at relatively higher force levels to provide similar pressures. For example, a force of 20 lbs and a wire diameter of 0.013 inch results in a pressure of about 150,000 psi, while a force of 47 lbs and a wire diameter of 0.020 inch also results in a pressure of about 150,000 psi. In an embodiment, the wire segments so joined may have about the same diameter (e.g., within about 25%, within about 10%, within about 5%, or within about 1% of one another). In one embodiment, the wire segment diameters may be approximately equal (e.g., both about 0.013 inch).

The baseline force may be applied while electrical (e.g., DC, AC, or both) current is applied to the segments. The value of the baseline force may be substantially constant over the period over which it is applied. As weld energy is input in the form of applied electrical (e.g., DC, AC, or both) current, the regions adjacent the corresponding ends which are pressed together will begin to soften as the temperature increases. At some point, these regions will begin to collapse towards one another (i.e., solid state deformation) as setdown or axial displacement occurs, as a result of solid-state deformation.

Electrical weld energy input (i.e., application of electrical (e.g., DC, AC, or both) current) may last from about 1 ms to about 100 ms, from about 5 ms to about 50 ms, or from about 10 ms to about 30 ms. The value of the applied current may depend on duration of the input, as well as the dimensions and material characteristics of the segments being joined together. In one embodiment, the applied current may be from about 0.01 kA to about 0.1 kA, from about 0.05 kA to about 0.08 kA, or from about 0.06 kA to about 0.07 kA. Of course, larger or smaller values than these ranges may be appropriate where the dimensions and/or material characteristics of the segments so dictate. Applied current may be DC current, AC current, or both. For example, an embodiment may employ a high frequency inverter power source which may provide a DC pulse that may include high frequency AC overlaid on it. Such a power source may differ from standard AC in that the high frequency potential may not completely reverse polarity.

The follow up force (e.g., axial) is applied after solid-state deformation (setdown) begins, but before such deformation has completed. The follow up force may be applied after some (e.g., most or all) of the electrical weld energy has been delivered (e.g., the electrical (e.g., DC, AC, or both) current delivery may have stopped). In one embodiment, there is a gap between when electrical weld energy input stops and the start of application of the follow up force. For example, application of the follow up force may begin from about 0.5 ms to about 10 ms after the end of electrical (e.g., DC, AC, or both) current delivery, from about 2 ms to about 8 ms after the end of electrical (e.g., DC, AC, or both) current delivery, or from about 3 ms to about 5 ms after the end of electrical (e.g., DC, AC, or both) current delivery.

As with the baseline force, the value of the applied follow up force may depend on the material characteristics and dimensions (e.g., diameter) of the segments being directly joined together. In one embodiment, the follow up force may be from about 2 lbs to about 200 lbs, from about 10 lbs to about 100 lbs, from about 20 lbs to about 60 lbs, or from about 30 lbs to about 40 lbs. The follow up force and the cross-sectional thickness of the wire segments may result in a pressure at the interface of the segments from about 50,000 psi to about 750,000 psi, from about 125,000 psi to about 450,000 psi, or from about 175,000 to about 350,000 psi. For example, a follow up force of 35 lbs and a wire diameter of 0.013 inch results in a pressure of about 265,000 psi. In one embodiment, the follow up force and/or the pressure provided by the follow up force is from about 10% greater to about 200% greater than the baseline force (or baseline pressure), from about 25% greater to about 150% greater than the baseline force (or baseline pressure), or from about 50% greater to about 100% greater than the baseline force (or baseline pressure).

Figure 4:
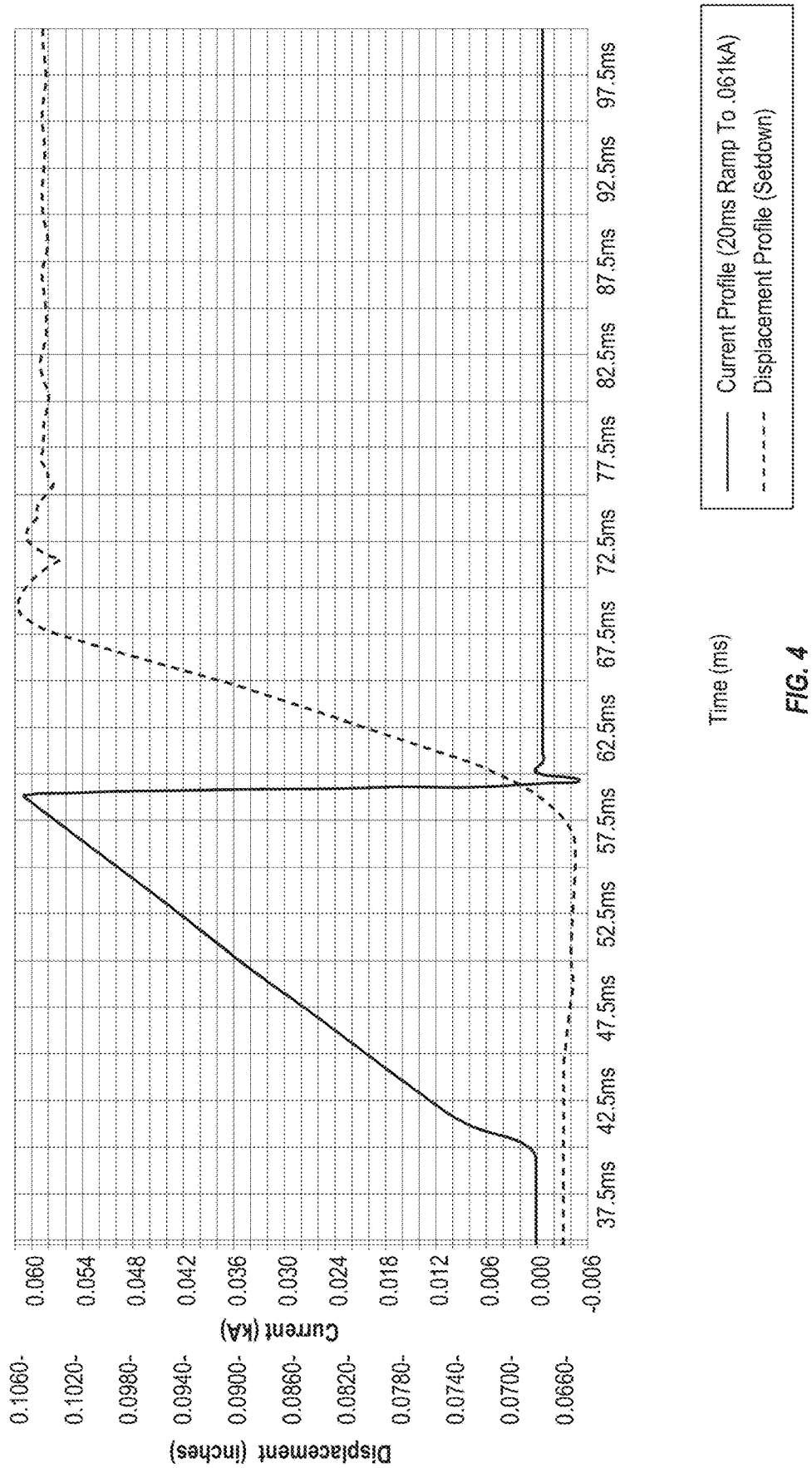
FIG. 4 is a plot showing an electrical weld energy input profile and an axial displacement profile for butt welding dissimilar guide wire segments without application of any follow up axial force.
Figure 5:
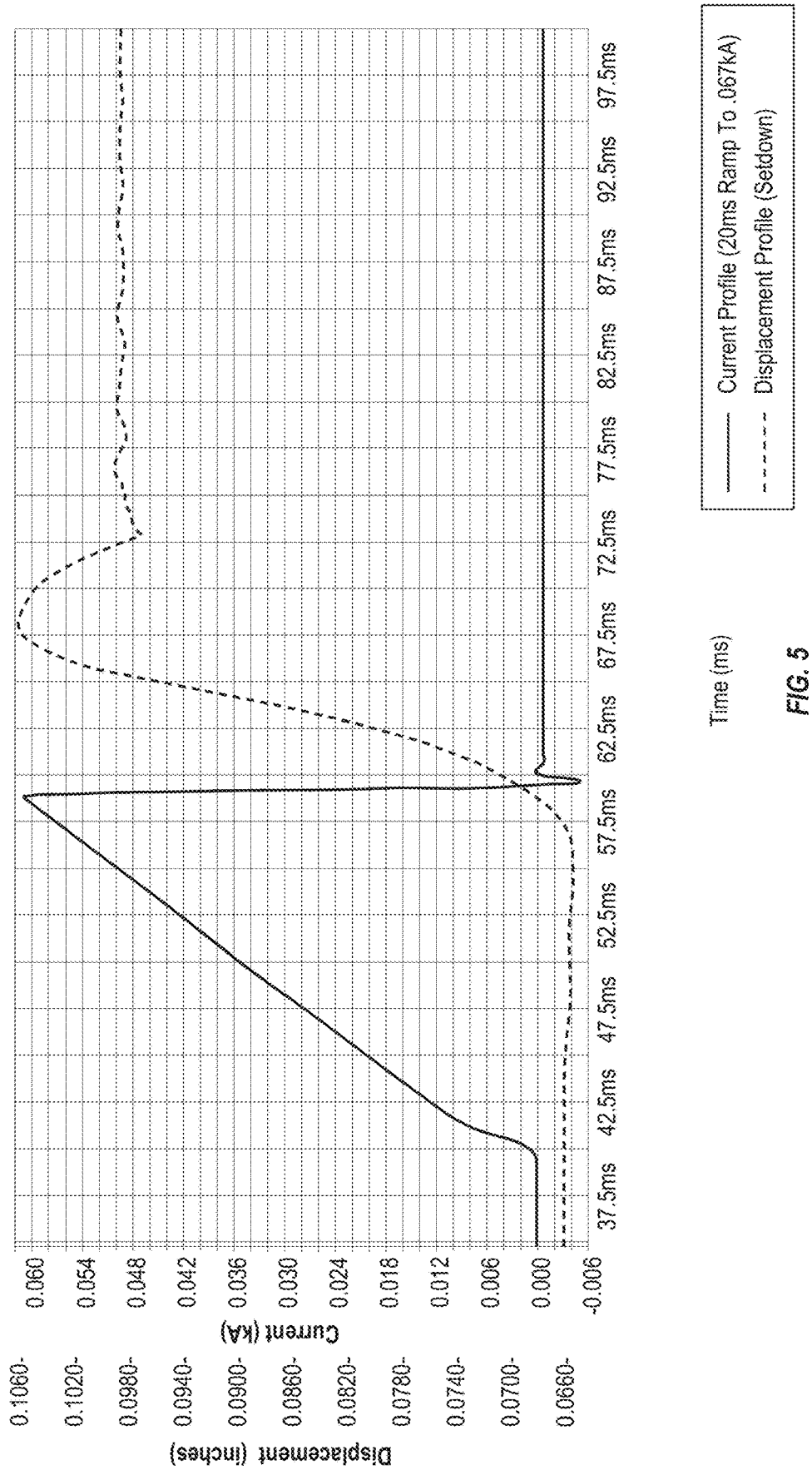
FIG. 5 is a plot showing an electrical weld energy input profile and an axial displacement profile for butt welding dissimilar guide wire segments with application of follow up axial force.

FIGS. 4 and 5 plot electrical weld energy input and axial deformation profiles for directly butt welding a stainless steel proximal guide wire portion to a nitinol distal guide wire portion. Each portion had a diameter of about 0.013 inch. The profiles shown in FIG. 4 are without application of a follow up axial force, while the profiles shown in FIG. 5 are with application of a follow up axial force.

Figure 8A:
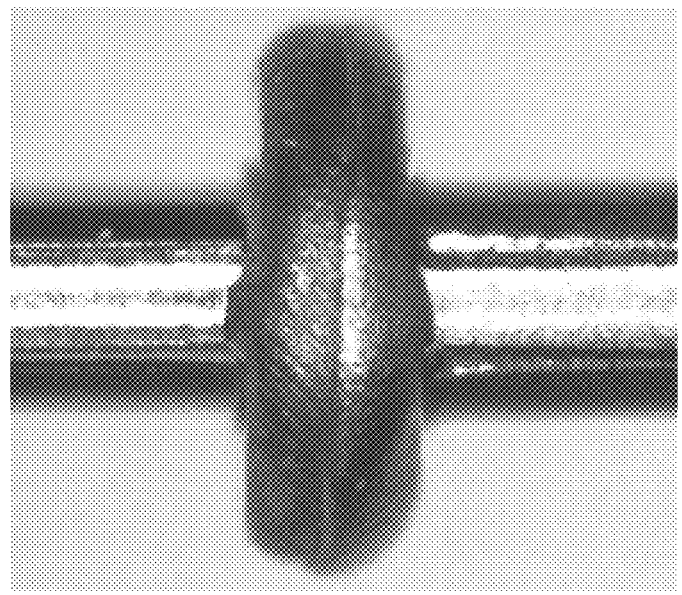
FIG. 8A is a photograph of a weld nugget formed under the conditions associated with FIG. 4.

As seen in FIG. 4, electrical weld energy input was ramped over a period of 20 ms to a value of about 0.061 kA. The baseline axial force applied was at a value of 20 lbs. In FIG. 5, current application was similarly ramped over a period of 20 ms to a value of about 0.061 kA. The baseline axial force applied was also at a value of 20 lbs. About 4 ms after current delivery stopped, once axial displacement (setdown) had begun, the force was increased to 35 lbs. In FIG. 4, the total axial displacement or setdown was 0.0381 inch. In FIG. 5, the total axial displacement or setdown was 0.0402 inch. The greater axial displacement value of FIG. 5 corresponds to a weld nugget of thinner cross-sectional thickness and greater transverse cross-sectional diameter than that of FIG. 4. Photographs of the two weld nuggets so formed are shown in FIGS. 8A and 83B.

Figure 6:
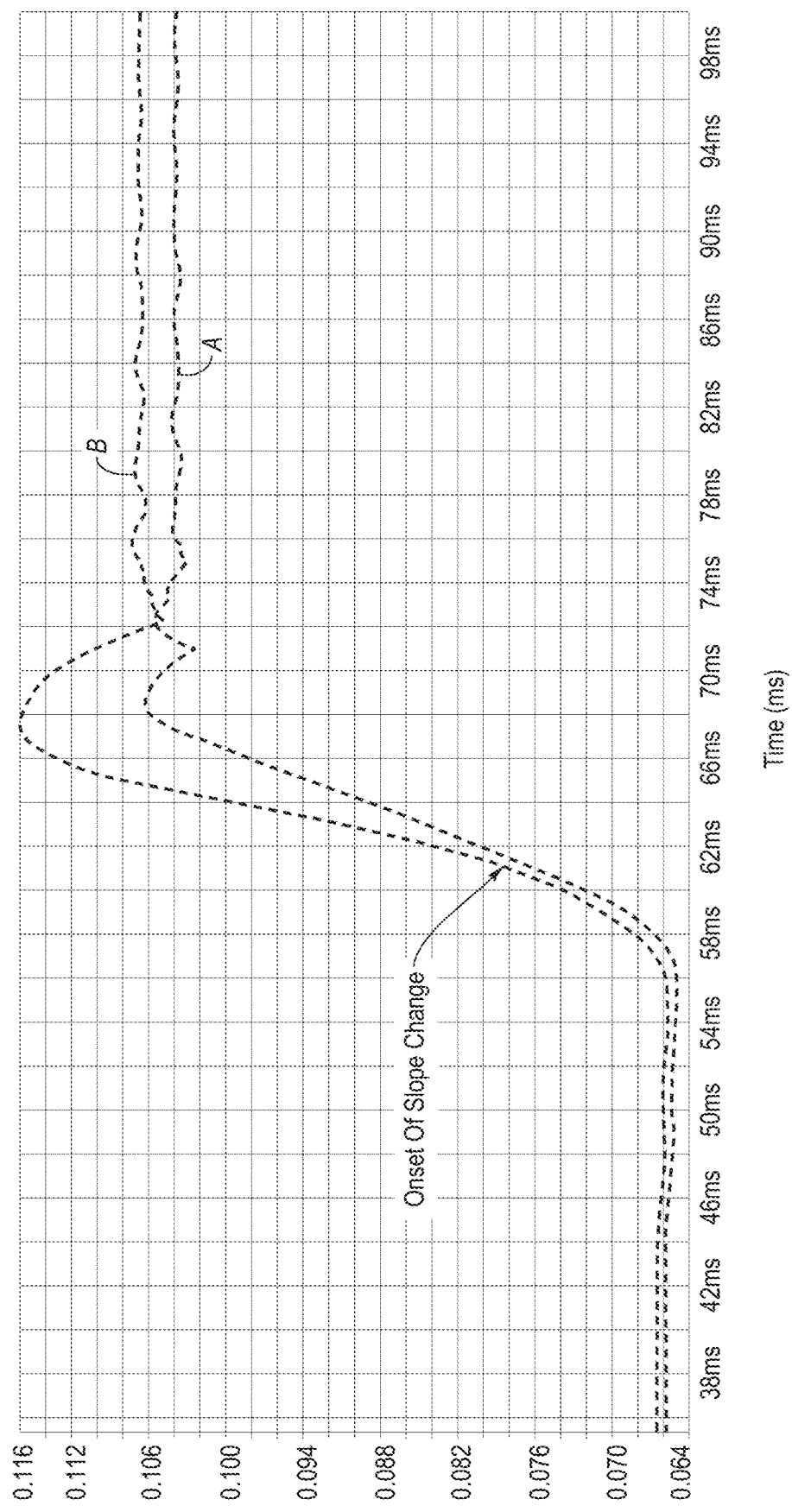
FIG. 6 is a plot showing the axial displacement profiles of FIGS. 4 and 5 on a single plot, illustrating the change in slope of the axial displacement profile where follow up force is applied.

FIG. 6 shows the axial displacement profiles of FIGS. 4 and 5 on the same plot. The plotted profiles A and B begin substantially parallel to one another, with the divergence beginning at the point where the follow up axial force is applied in example B and not example A.

Application of a follow up axial force of greater value than the baseline axial force has been found to eliminate unacceptable variability in weld strength that is due to mechanical rebounding. Rebounding is believed to be a natural consequence of the sudden collapse of weld material when heated abruptly under an axial load. For example, rebounding may occur with the abrupt halt of axial deformation during formation of the weld nugget as a sliding wire grip that grips the respective wire segments reverses direction and thereby applies a varying load to the newly formed weld. This may result in brief tensile loading on the weld, even though only compressive loading is intended. While such mechanical rebounding is present in both of the configurations described in conjunction with FIGS. 4 and 5, a larger diameter weld nugget (associated with FIG. 5), including increased cross-sectional area at the interface between the dissimilar, incompatible materials serves to better accept such a transitory tensile load without pulling the weld apart or resulting in hidden damage within the weld nugget that might later lead to failure of the guide wire at the weld. In addition, application of the follow up force serves to squeeze and thereby extract heat from the weld nugget while substantially enlarging its cross-sectional area. Extraction of heat serves to decrease the temperature of the weld nugget, particularly its interface, thereby raising its strength and further improving its resistance to rebounding forces.

Figure 7A:
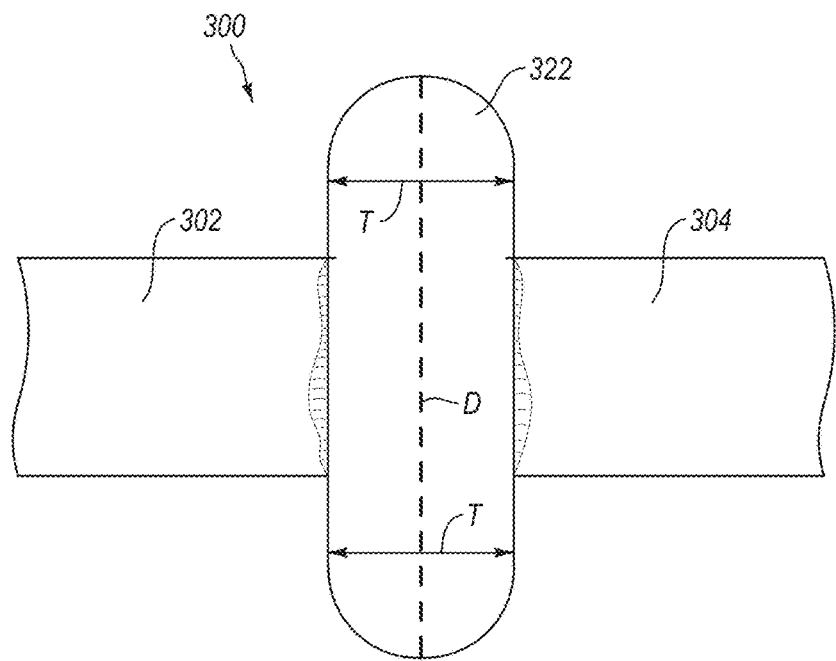
FIG. 7A is a close up side elevation view showing the heat affected zone and weld nugget formed under the conditions associated with FIG. 4, without application of follow up force.
Figure 7B:
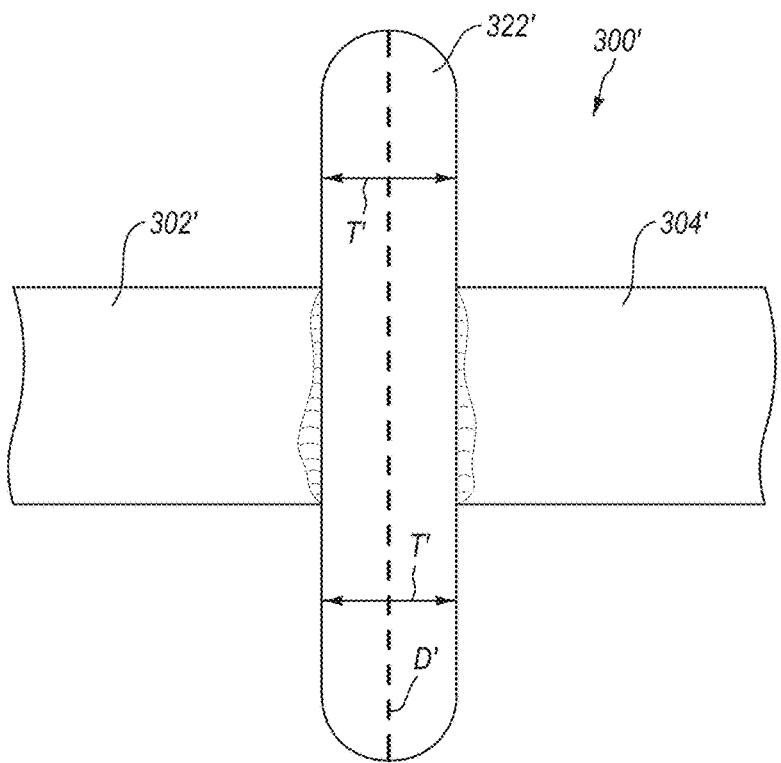
FIG. 7B is a side elevation view showing the heat affected zone and weld nugget formed under the conditions associated with FIG. 5, including application of follow up force.

FIG. 7A depicts an exemplary proximal and distal portion 302 and 304, respectively of a multi-segment guide wire 300 in the vicinity of the formed weld nugget. FIG. 7A corresponds to FIG. 4, which does not include application of any follow up force. FIG. 7B depicts proximal and distal portions 302' and 304', respectively of a multi-segment guide wire 300' formed with application of a follow up axial force (corresponding to FIG. 5). These depictions correspond to the actual photographs shown in FIGS. 8A and 8B. In each, the weld nugget 322 and 322' is seen disposed surrounding the interface where the respective proximal and distal portions are joined together. In one embodiment, weld nugget 322', formed under conditions in which a larger follow up axial force is applied, exhibits a diameter D' that is at least about 5% greater, at least about 10% greater, or about 15% greater to about 25% greater than diameter D that would be produced without application of the follow up axial force. Stated another way, where the diameter D' is about 20% larger in weld nugget 322' than diameter D of weld nugget 322, the cross-sectional area of weld nugget 322' will be about 45% greater than the cross-sectional area of weld nugget 322. This significantly increased cross-sectional area (i.e., increased bonding area) better resists undesirable tensile loading due to mechanical rebounding.

Related to this characteristic of increased diameter and cross-sectional area, weld nugget 322' may have an average thickness T' that is from about 10% smaller to about 50% smaller, about 15% smaller to about 35% smaller, or about 20% smaller to about 30% smaller than thickness T that would be produced without application of the follow up axial force.

Figure 8B:
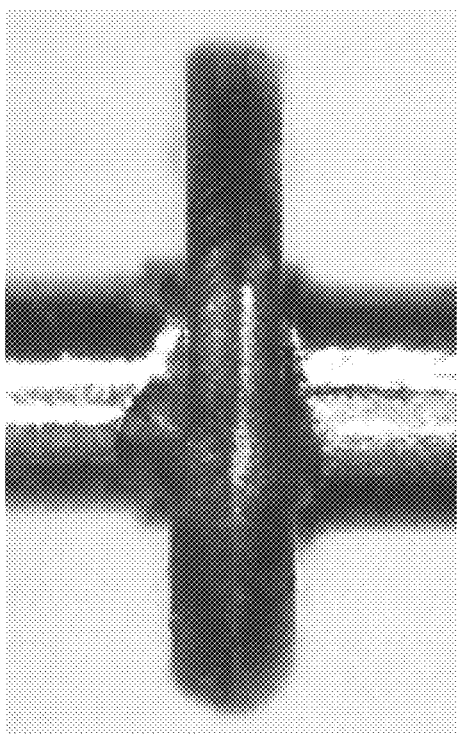
FIG. 8B is a photograph of a weld nugget formed under the conditions associated with FIG. 5.
Figure 9A:
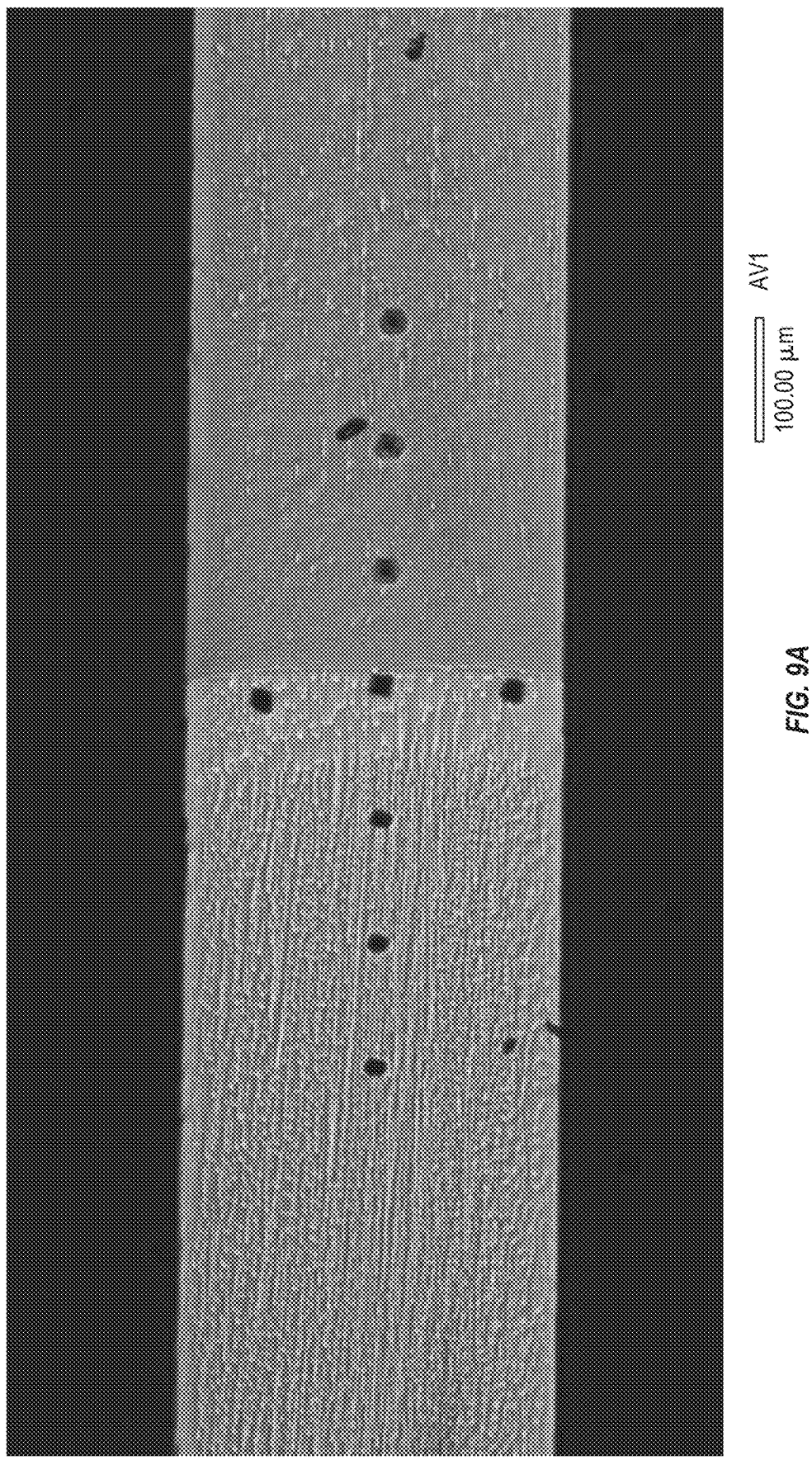
FIGS. 9A-9E show images of multi-segment guide wires according to the present disclosure.
Figure 9B:
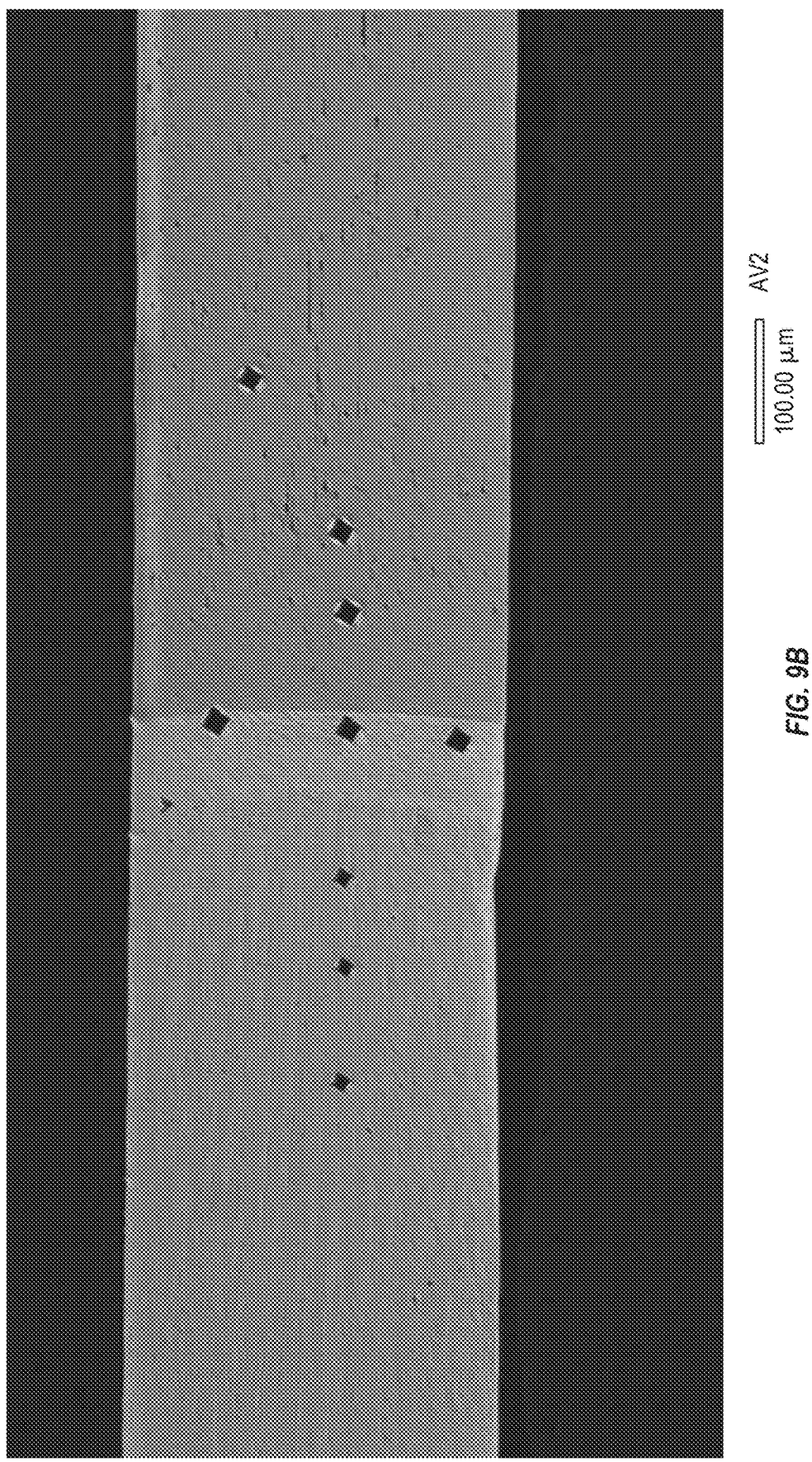
Figure 9C:
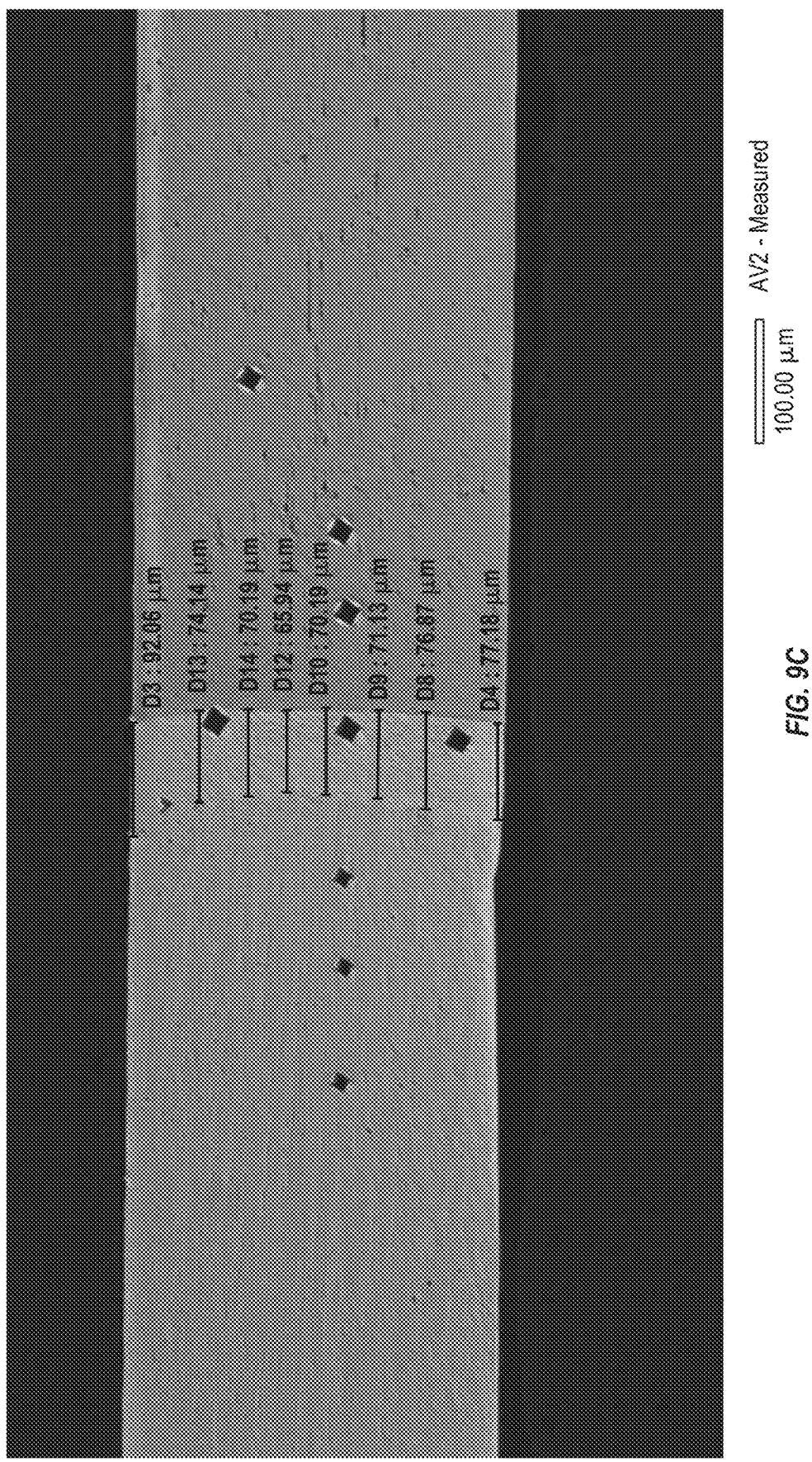
Figure 9D:
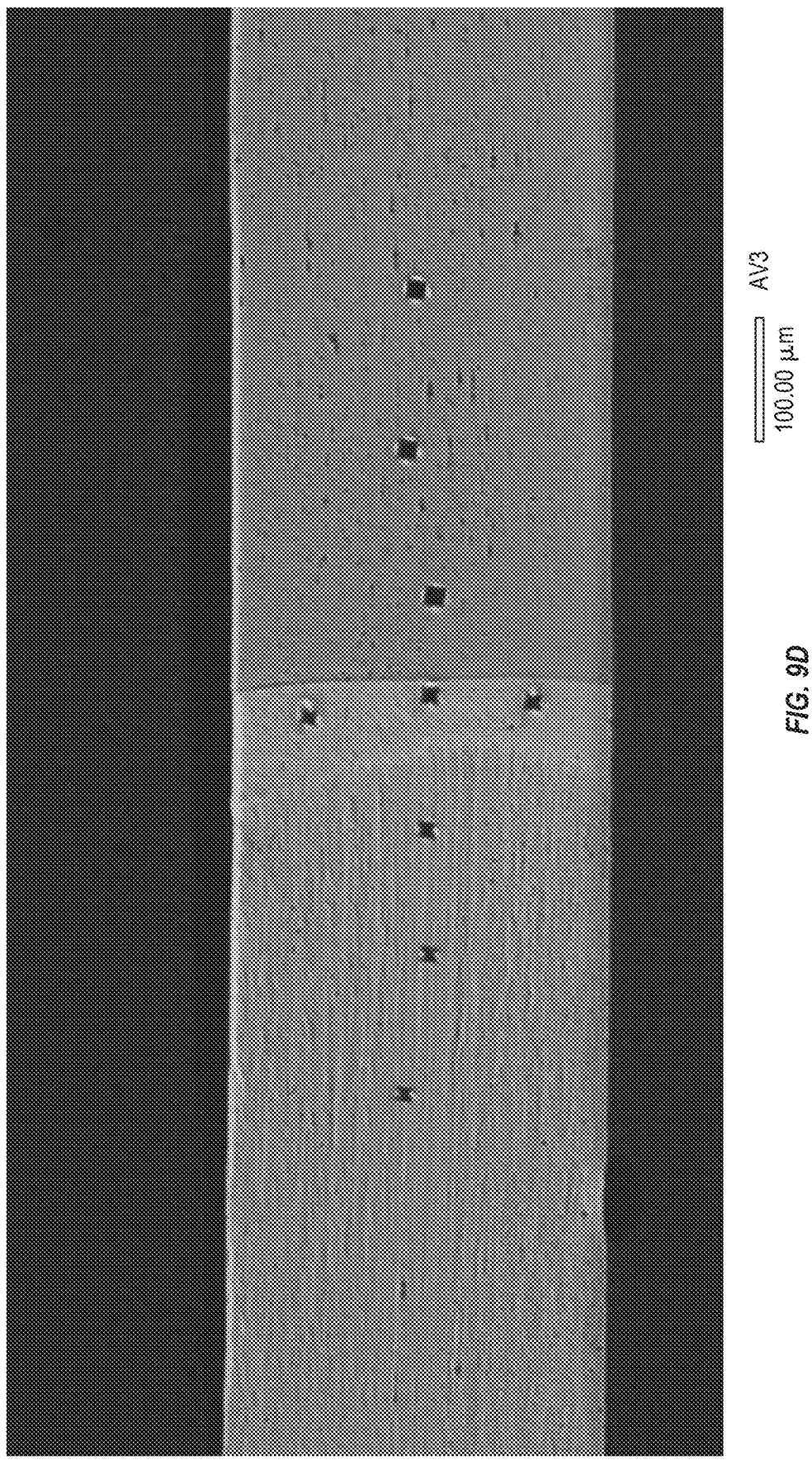
Figure 9E:
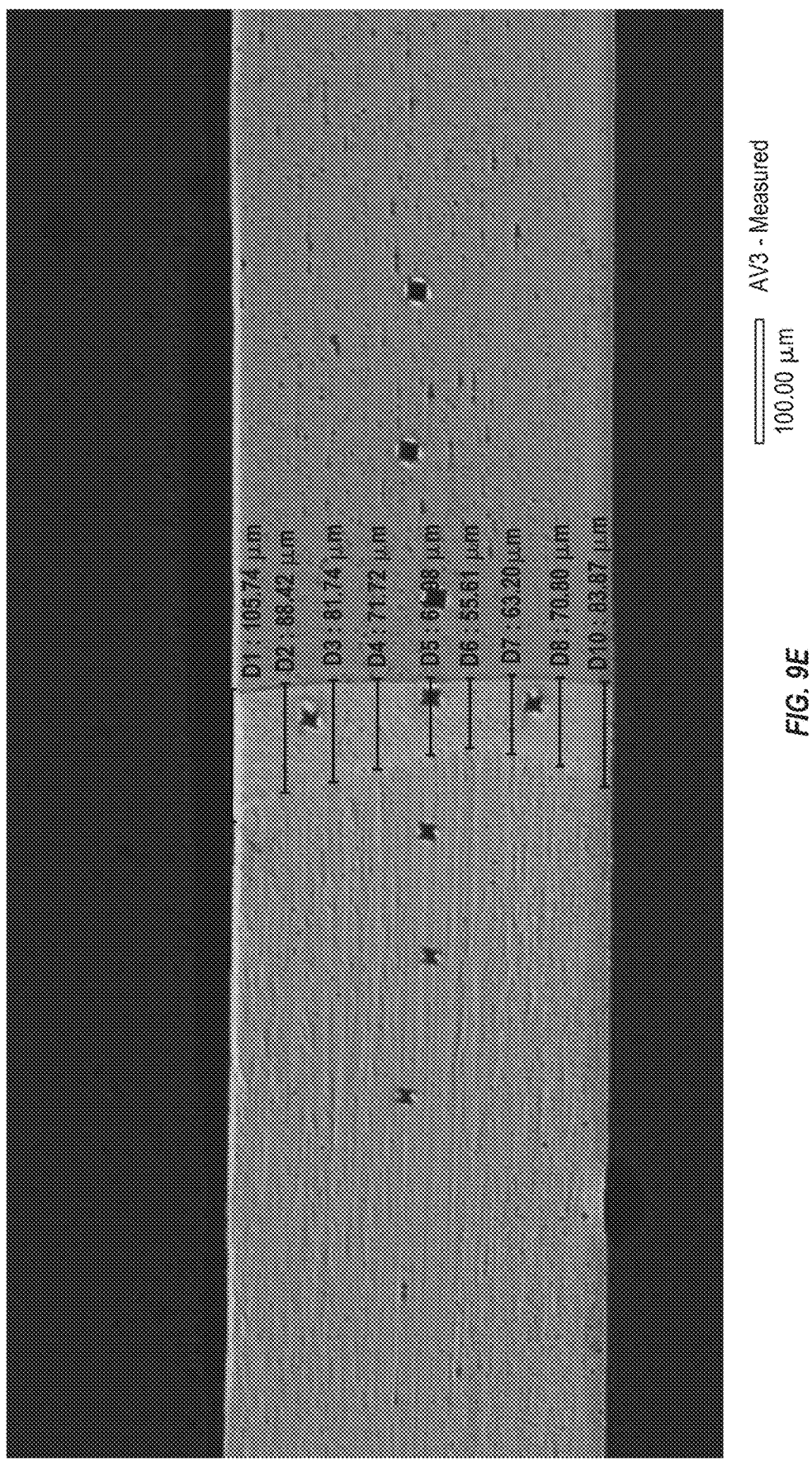
Figure 10A:
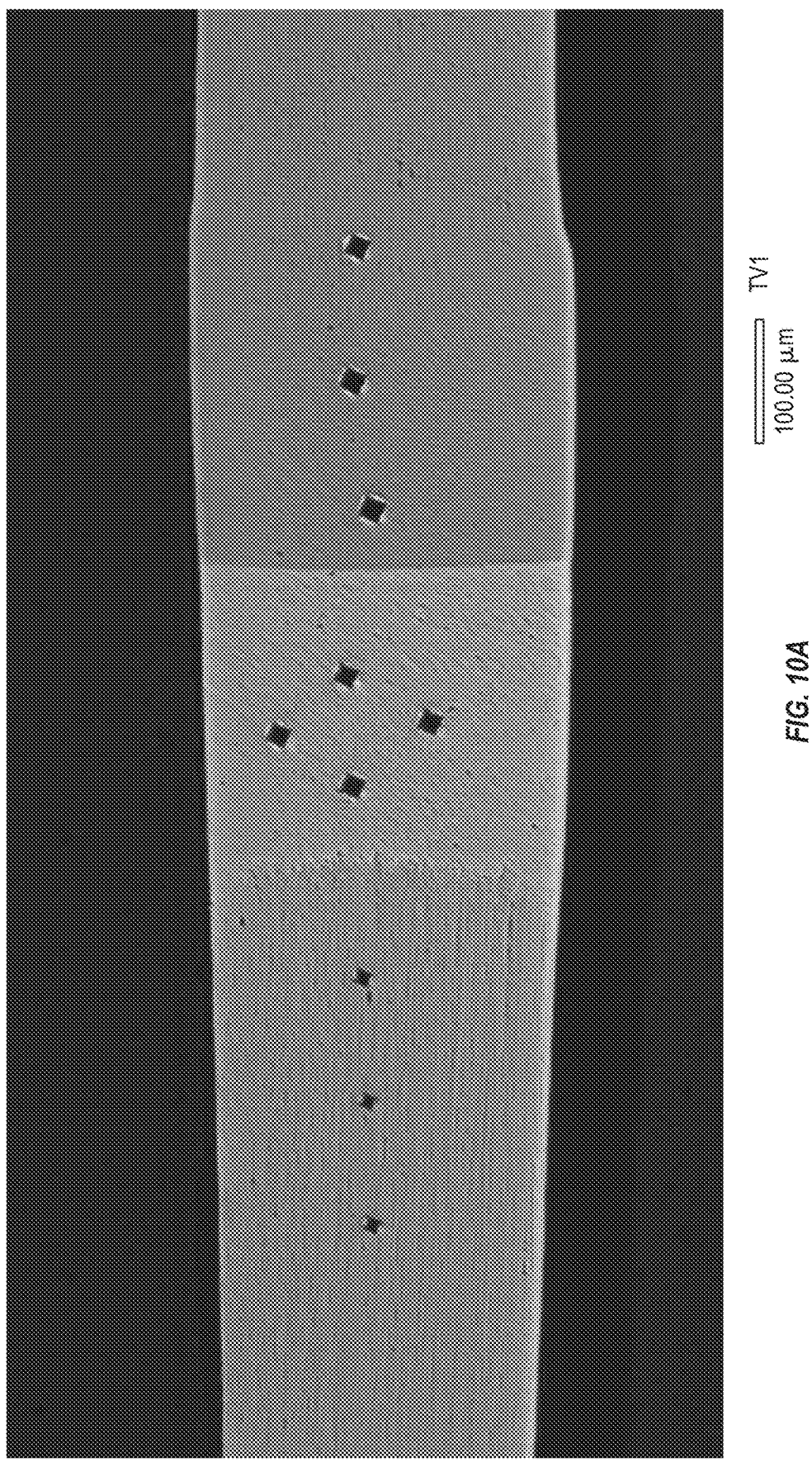
FIGS. 10A-10F show images of Terumo guide wires.
Figure 10B:
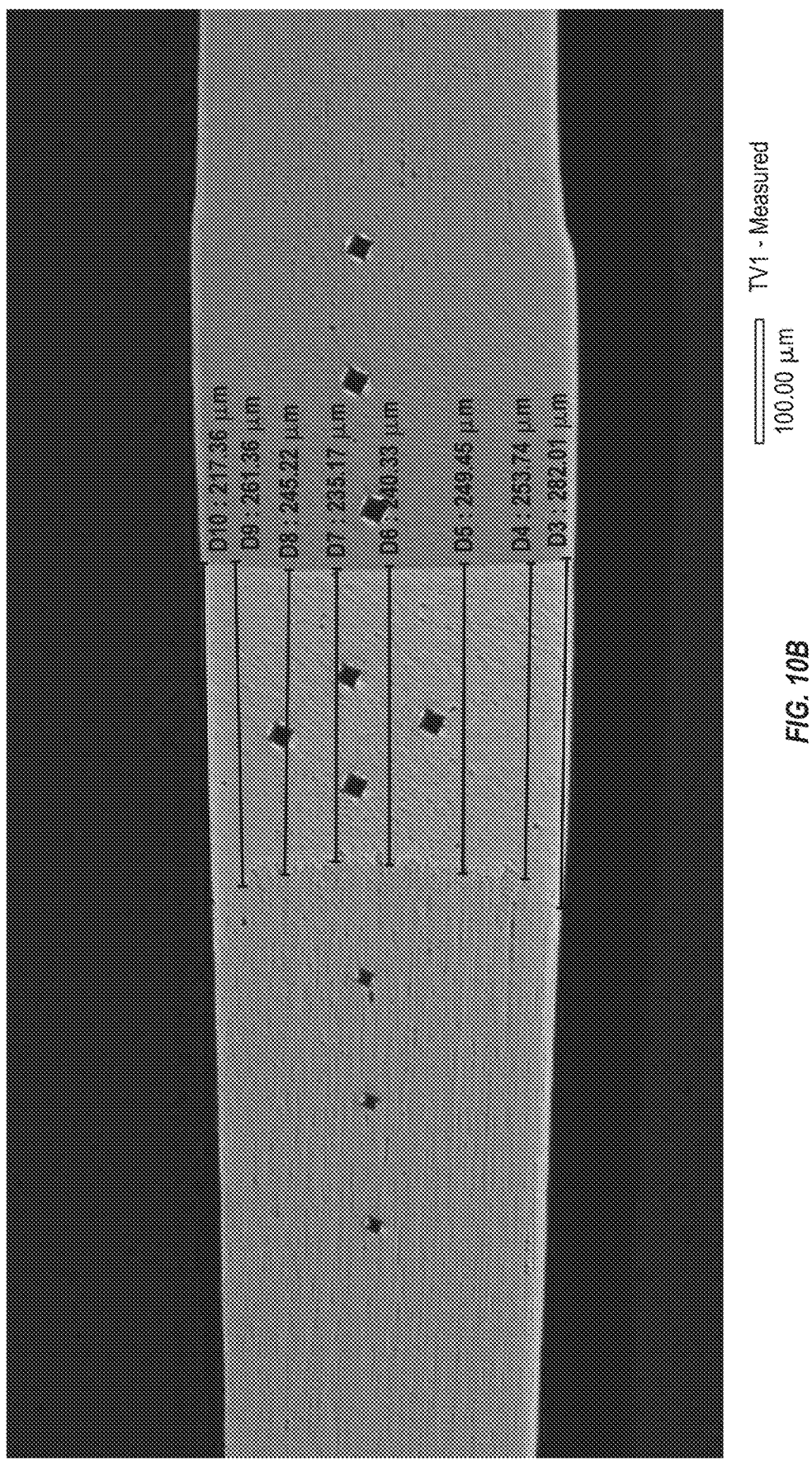
Figure 10C:
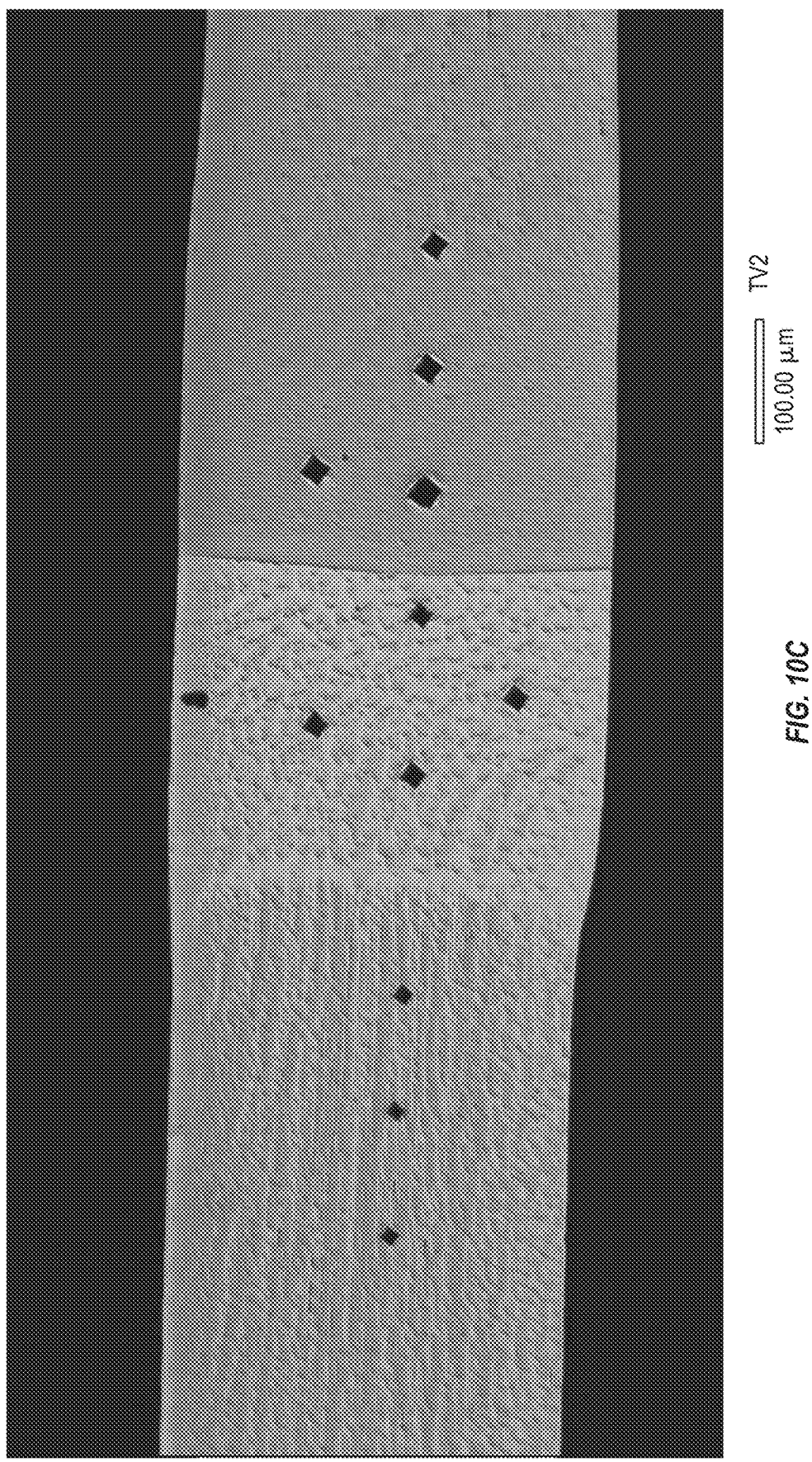
Figure 10D:
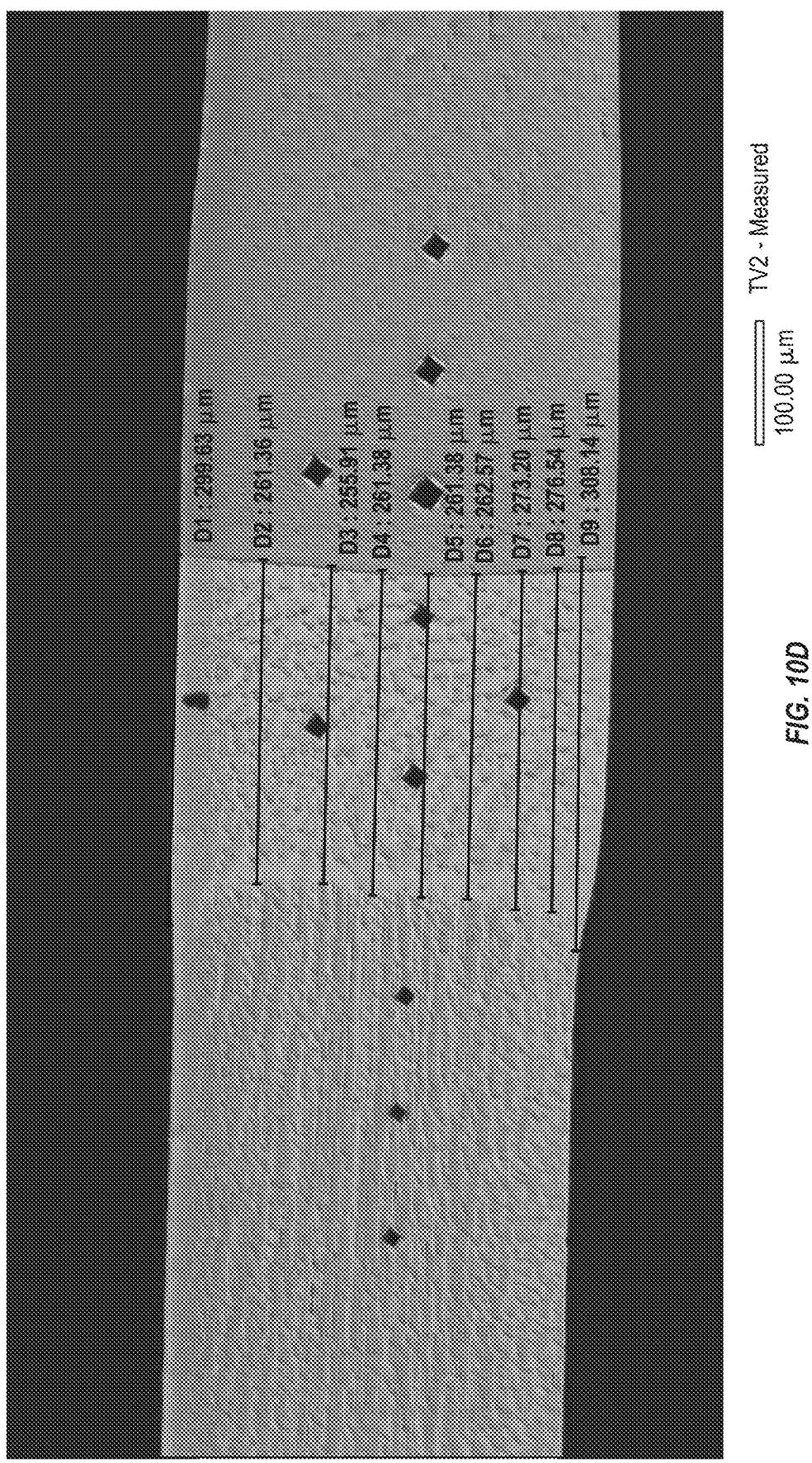
Figure 10E:
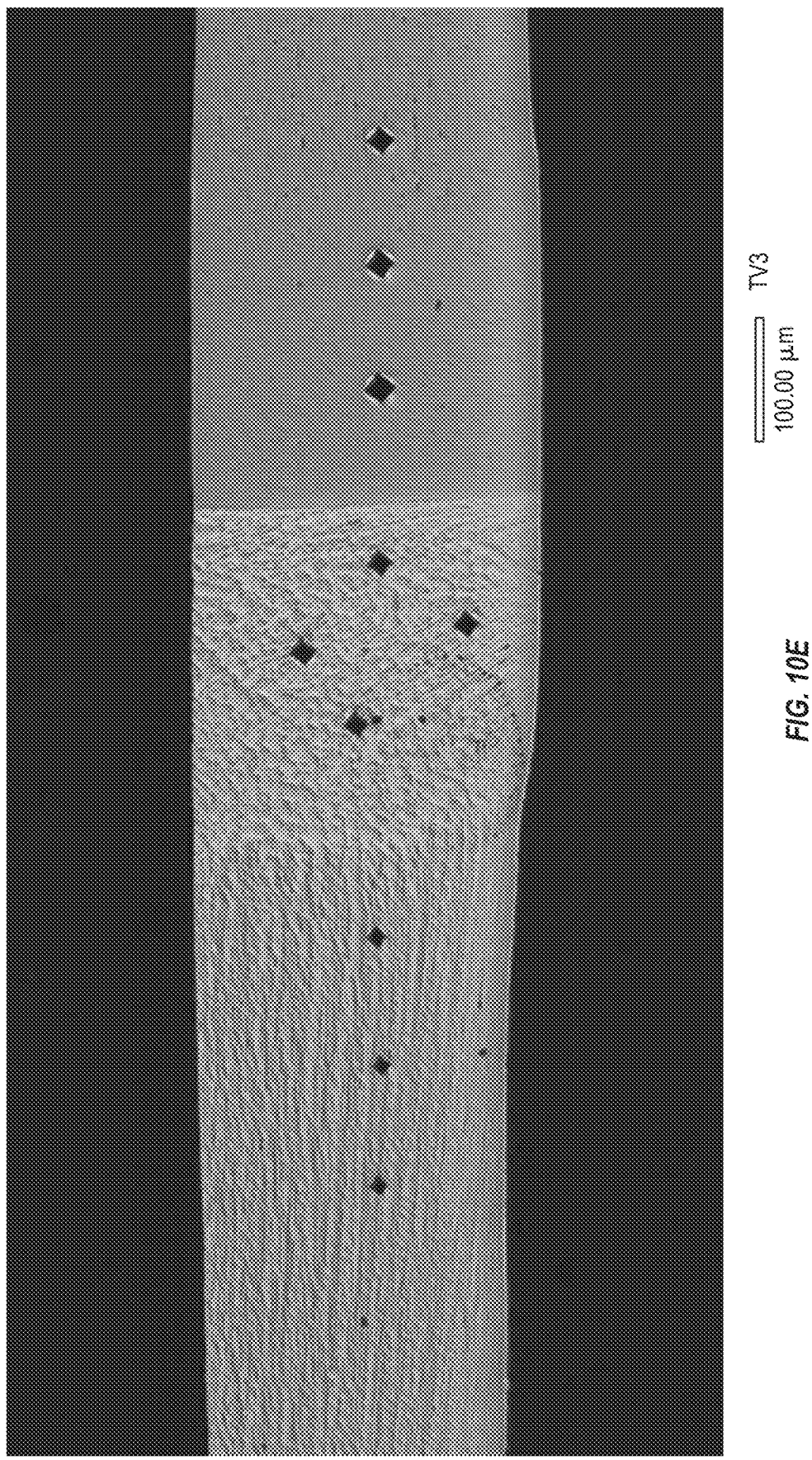
Figure 10F:
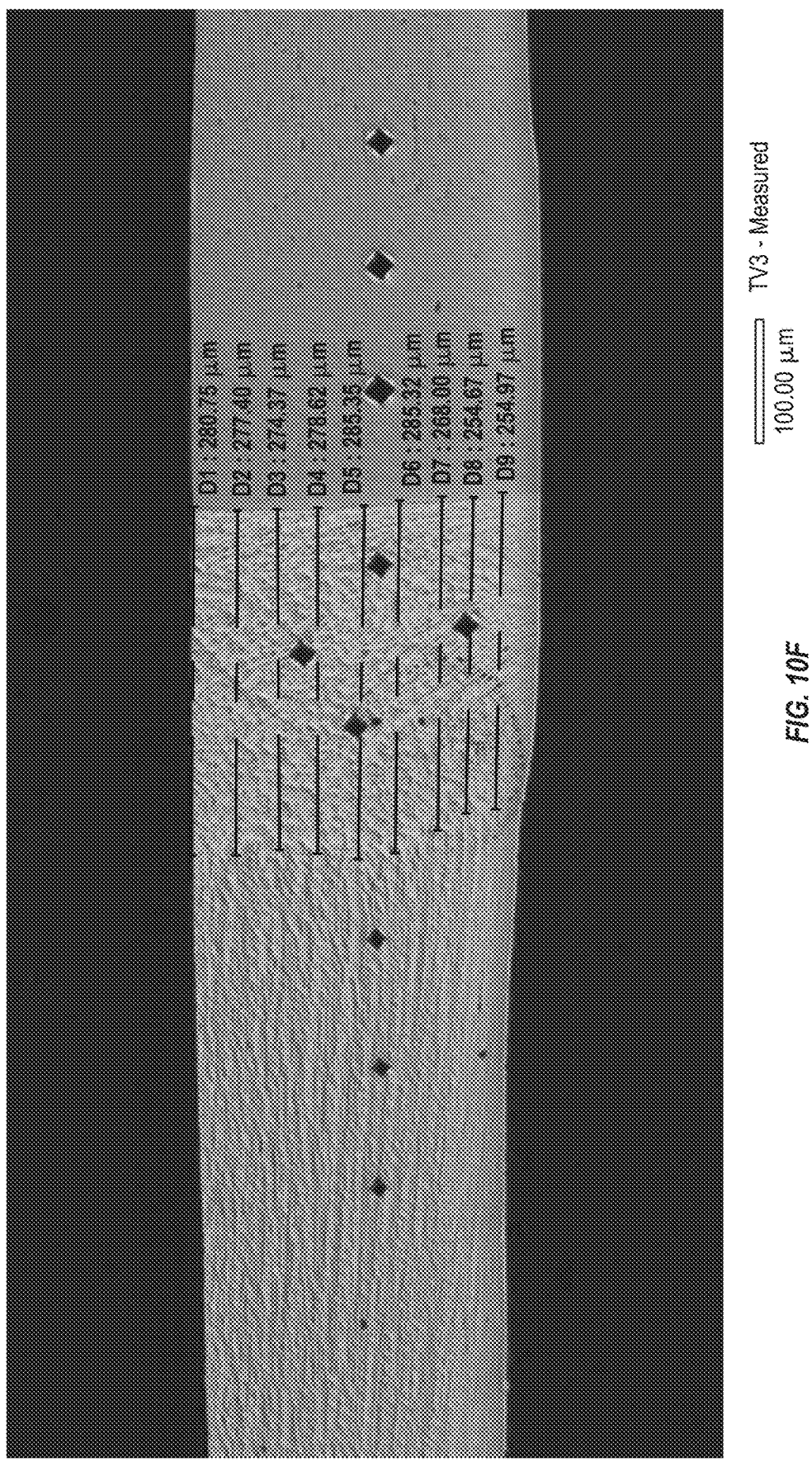

The actual weld nuggets shown in FIGS. 8A and 8B exhibited an average thickness of 0.22 mm without application of a follow up force, and an average thickness of 0.15 mm with application of a follow up force. The resulting diameter shown in FIG. 8B was 20% larger than that shown in FIG. 8A, providing an increase in cross-sectional bonded surface area of 45%.

While the embodiments described in FIGS. 4-8B are shown as being carried out under conditions in which the corresponding ends of the segments or portions are shaped and oriented to provide a butt joint as a result of the weld, it will be understood that other welded joint configurations, including but not limited to butt joints, overlap joints, joints including corresponding oblique angled ends, and combinations thereof may also be employed. Various alternative joint configurations that may be employed are shown in U.S. Pat. No. 7,998,090, herein incorporated by reference in its entirety.

Once the two segments have been joined together, the weld nugget disposed therebetween can be removed by grinding. For example, the majority of the excess weld nugget material extending laterally beyond the diameter of the adjacent proximal and distal segments may be ground away in a centerless grinding operation. Any remaining excess metal may be removed while grinding the entire distal core wire profile. In addition to simply allowing direct joining of dissimilar metallic materials to one another with a solid-state weld joint, multi-segment guide wires formed as described herein with application of an increased follow up force exhibit characteristics allowing them to be identified as having been produced according to such methods herein described. For example, in one embodiment, the resulting multi-segment guide wire includes a heat affected zone corresponding to the location of the weld nugget. In one embodiment, such a multi-segment guide wire may have a heat affected zone that has a thickness of less than about 0.20 mm, less than about 0.18 mm, or from about 0.15 mm to about 0.18 mm in thickness. Such reduced thickness heat affected zones provide improved kink resistance. The heat affected zone may also exhibit unique hardness characteristics as a result of the heat affected zone having undergone greater levels of solid state deformation arising from the follow up force. Specifically, the heat affected zone is expected to be narrower and exhibit a lesser degree of softening as compared with welds created without a follow up force.

Comparative measurements of the heat affected zone (e.g., the weld width) were carried out on multi-segment guide wires according to the present disclosure as compared to Terumo guide wires. Measurement of microhardness impressions within the stainless steel portion, the nickel-titanium portion, and the heat affected weld zone therebetween were taken using Vickers hardness testing. Each Vickers hardness measurement was made using 100 grams of force (HV100). Three measurements within each region were obtained. The results are shown in Tables 1A and 1B. AV1, AV2, and AV3 refer to multi-segment guide wires according to the present disclosure. T1, T2, and T3 refer to hardness tested Terumo guide wires.

TABLE 1A

| Region | AV1 (HV) | AV2 (HV) | AV3 (HV) | T1 (HV) | T2 (HV) | T3 (HV) |
| --- | --- | --- | --- | --- | --- | --- |
| $NiTi_1$ | 393 | 389 | 376 | — | 315 | 334 |
| $NiTi_2$ | 385 | 371 | 381 | 279 | 292 | 329 |
| $NiTi_3$ | 379 | 381 | 352 | 290 | 274 | 297 |
| $Weld_1$ | 377 | 359 | 420 | 380 | 390 | 393 |
| $Weld_2$ | 383 | 352 | 429 | 364 | 389 | 393 |
| $Weld_3$ | 361 | 367 | 433 | 388 | 427 | 398 |
| $SS_1$ | 702 | 688 | 666 | 715 | 649 | 639 |
| $SS_2$ | 737 | 708 | 701 | 698 | 701 | 704 |
| $SS_3$ | 728 | 692 | 730 | 728 | 713 | 727 |

TABLE 1B

| Region (Average) | AV1 (HV) | AV2 (HV) | AV3 (HV) | T1 (HV) | T2 (HV) | T3 (HV) |
| --- | --- | --- | --- | --- | --- | --- |
| NiTi | 386 | 380 | 370 | 285 | 294 | 320 |
| Weld | 374 | 359 | 427 | 370 | 388 | 391 |
| SS | 722 | 696 | 699 | 714 | 688 | 690 |

Measurements of the heat affected zone (e.g., weld width) within the stainless steel portion of the multi-segment guide wire were also obtained, as presented in Table 1C. The total length of the heat affected zone, including in the nitinol portion, are approximately double the shown values.

TABLE 1C

|  | AV1 | AV2 (μm) | AV3 (μm) | T1 (μm) | T2 (μm) | T3 (μm) |
|---|---|---|---|---|---|---|
| Weld Width | — | 65-92 | 63-100 | 235-285 | 255-308 | 254-285 |

FIGS. 9A-9E show images of the multi-segment guide wires AV1-AV3 that were measured. FIGS. 10A-10F show images of the Terumo guide wires T1-T3.

Comparative strength testing was performed on multi-segment guide wires formed according to methods described above in conjunction with FIGS. 4-5. Multi-segment guide wires formed with and without application of a follow up axial force were subjected to destructive rotary bend testing (essentially a low-cycle fatigue test). Tensile testing may not always correlate to actual performance in bending conditions (which exist during use of the guide wires). For example, while a welding process may produce components that exhibit acceptable, even high tensile test values, the inventors have found that some such welded components perform poorly when subjected to bending.

Rotary bend testing better approximates use conditions, and provides a better measurement of weld strength during use. In rotary bend testing, the weld of each guide wire was simultaneously bent to a 90° and rotated one complete revolution (360°) in order to challenge all locations around the weld joint perimeter. The test design ensures that the weld interface will reside near the onset of the 90° bend, and thus participate in the curvature. As the applied force incrementally increases during testing, the radius of curvature within the turn becomes tighter, thereby increasing the bend severity and further challenging the weld interface. Each rotary bend test result was recorded in psi, representing the actual air pressure being applied, at the moment of failure, to a piston used to apply the force. The cross-sectional area of the piston was about 0.1 inch, thus the actual applied force can be calculated by multiplying any recorded psi value by 0.1. The results are shown below in Table 2:

TABLE 2

|  | N | Min (psi) | Max (psi) | Range (psi) | Mean (psi) | St. Dev. (psi) | Cpk |
|---|---|---|---|---|---|---|---|
| (A) Without Follow Up Force | 405 | 2.00 | 4.70 | 2.70 | 3.49 | 0.46 | 0.94 |
| (B) With Follow Up Force | 307 | 2.90 | 4.80 | 1.90 | 3.94 | 0.33 | 1.74 |

Each of groups A and B were formed in a manner similar to one another, other than application of the follow up axial force in group B. Manufacturing conditions were as described above in conjunction with FIGS. 4-5. Group A had a significantly lower mean strength value, and the minimum strength value was only 2.0 psi, which is below a desired performance specification of 2.2 psi. Group B included a minimum strength value of 2.9 psi, well above the desired minimum of 2.2 psi. Cpk is a commonly employed index that quantifies how capable a process is of consistently meeting the desired specification. Higher values of Cpk correspond to better capability in consistently meeting the desired specification. Cpk is calculated by dividing the difference between the mean value and the specification by 3 standard deviations (i.e., (mean−2.2)/(3× stdev)). As is readily apparent from Table 2, the Cpk value for group B is nearly double the Cpk value for group A.

The comparative testing thus indicates that significantly greater consistency with respect to desired strength characteristics is achieved when forming the guide wires with application of a follow up axial force. This is particularly important where the guide wire exhibiting sub specification strength characteristics may not be readily recognizable through non-destructive quality control mechanisms. The inventive method of manufacture thus increases consistency within the manufactured guide wires, while decreasing any incidence of passing sub specification parts.

The embodiments of the present disclosure may be embodied in other specific forms without departing from its spirit or essential characteristics. The described embodiments are to be considered in all respects only as illustrative and not restrictive. Therefore, the scope of the disclosure is indicated by the appended claims rather than by the foregoing description. All changes that come within the meaning and range of equivalency of the claims are to be embraced within their scope.

The invention claimed is:

1. A multi-segment guidewire, the guidewire comprising:
a first elongate portion of a first material;
a second elongate portion of a second material having a higher modulus of elasticity than a material of the first elongate portion;
a solid-state deformation region disposed at a junction of a distal end of the first elongate portion and a proximal end of the second elongate portion, a distal-most end of the first elongate portion and a proximal-most end of the second elongate portion being free of any oxide layers, wherein the distal end and the proximal end are joined without melting of the first material and the second material.

2. The multi-segment device of claim 1, further comprising a heat affected zone at the solid-state deformation region, wherein the heat affected zone has an average thickness across the junction of the first elongate portion and the second elongate portion of less than about 0.20 mm.

3. The multi-segment device of claim 2, wherein the heat affected zone has a first thickness, in a direction aligned with a longitudinal axis of the multi-segment device, toward a center of the solid-state deformation region that is less than a second thickness, in the direction aligned with the longitudinal axis of the multi-segment device, toward a perimeter of the solid-state deformation region.

4. The multi-segment device of claim 1, wherein the distal-most end and the proximal-most end are each flattened and smooth.

5. The multi-segment device of claim 1, wherein the second elongate portion includes a tapered section.

6. The multi-segment device of claim 1, further comprising a coil disposed about at least a portion of the second elongate portion.

7. The multi-segment device of claim 1, wherein the second elongate portion includes a flattened, shapeable distal tip.

8. The multi-segment device of claim 1, wherein the second elongate portion comprises a pseudoelastic alloy including about 30 atomic percent to about 52 atomic percent titanium, up to about 10 atomic percent of one or more other alloying elements, with a balance of nickel.

9. The multi-segment device of claim 8, wherein the one or more other alloying elements comprises alloying elements selected from iron, cobalt, vanadium, platinum, palladium, copper, and combinations thereof.

10. The multi-segment device of claim 1, wherein the heat affected zone has an average thickness of less than about 0.18 mm.

11. The multi-segment device of claim 1, wherein the heat affected zone has an average thickness from about 0.15 mm to about 0.18 mm.

12. The multi-segment device of claim 1, wherein second elongate portion comprises a nickel-titanium alloy.

13. The multi-segment device of claim 1 wherein first elongate portion comprises stainless steel.

14. The multi-segment device of claim 1, wherein one of the first elongate portion and the second elongate portion comprises a nickel-titanium alloy and the other of the first elongate portion and the second elongate portion comprises stainless steel or a cobalt-chromium alloy.

15. The multi-segment device of claim 1, wherein the device exhibits a minimum strength value of at least 2.9 psi.

16. The multi-segment device of claim 1, wherein the device exhibits a mean strength value of at least 3.94 psi.

17. The multi-segment device of claim 1, wherein the device exhibits a Cpk value with respect to strength that is greater than 0.94.

18. The multi-segment device of claim 11, wherein the device exhibits a Cpk value with respect to strength that is at least about 1.74.

19. A multi-segment guidewire, the guidewire comprising:
   a first elongate portion of a first material, the first elongate portion comprising a smooth and flattened distal-most end;
   a second elongate portion of a second material having a higher modulus of elasticity than a material of the first elongate portion, the second elongate portion comprising a smooth and flattened proximal-most end;
   a solid-state deformation region including a junction of the distal-most end and the proximal-most end, each being free of any oxide layers, a distal end of the first elongate portion and a proximal end of the second elongate portion are joined without melting of the first material and the second material.

20. A multi-segment guidewire, the guidewire comprising:
   a first elongate portion of a first material, the first elongate portion comprising a smooth and flattened distal-most end;
   a second elongate portion of a second material having a higher modulus of elasticity than a material of the first elongate portion, the second elongate portion comprising a smooth and flattened proximal-most end;
   a solid-state deformation region including a junction of the distal-most end and the proximal-most end, each being free of any oxide layers, a distal end of the first elongate portion and a proximal end of the second elongate portion are joined without melting of the first material and the second material,
   wherein a heat affected zone is formed in the solid-state deformation region, the heat affected zone having an average thickness across the junction of the first elongate portion and the second elongate portion of less than about 0.20 mm, the heat affected zone having a first thickness toward a center of the solid-state deformation region, and in a direction aligned with a longitudinal axis of the multi-segment device, that is less than a second thickness toward a perimeter of the solid-state deformation region, and in the direction aligned with the longitudinal axis of the multi-segment device.

* * * * *